United States Patent
Erickson et al.

(10) Patent No.: US 12,115,102 B2
(45) Date of Patent: Oct. 15, 2024

(54) OPHTHALMIC IMPLANT FOR DELIVERING THERAPEUTIC SUBSTANCES

(71) Applicant: ForSight Vision4, Inc., South San Francisco, CA (US)

(72) Inventors: Signe Erickson, South San Francisco, CA (US); Randolph E. Campbell, South San Francisco, CA (US); Darren Doud, South San Francisco, CA (US)

(73) Assignee: ForSight Vision4, Inc., South San Francisco, CA (US)

( * ) Notice: Subject to any disclaimer, the term of this patent is extended or adjusted under 35 U.S.C. 154(b) by 170 days.

(21) Appl. No.: 17/974,228

(22) Filed: Oct. 26, 2022

(65) Prior Publication Data

US 2023/0145887 A1    May 11, 2023

Related U.S. Application Data

(63) Continuation of application No. 16/514,128, filed on Jul. 17, 2019, now Pat. No. 11,510,810, which is a
(Continued)

(51) Int. Cl.
*A61F 9/00* (2006.01)
*A61M 39/02* (2006.01)

(52) U.S. Cl.
CPC ....... *A61F 9/0017* (2013.01); *A61M 39/0208* (2013.01)

(58) Field of Classification Search
CPC .......................... A61F 9/0017; A61M 39/0208
See application file for complete search history.

(56) References Cited

U.S. PATENT DOCUMENTS

| 2,564,977 A | 8/1951 | Hu et al. |
| 2,585,815 A | 2/1952 | McLintock |

(Continued)

FOREIGN PATENT DOCUMENTS

| CA | 2807535 A1 | 2/2012 |
| CA | 2807554 A1 | 2/2012 |

(Continued)

OTHER PUBLICATIONS

"MAbPac SCX-10 Column for Monoclonal Antibody Variant Analysis." Dionex.Aug. 2010. [http://www.dionex.com/en-us/webdocs/87008-DS-MAbPac-SCX-10-Column-20Aug2010-LPN2567-03.pdf]. Web. Retrieved May 2012. 4 pages.
(Continued)

*Primary Examiner* — Bradley J Osinski
(74) *Attorney, Agent, or Firm* — Mintz Levin Cohn Ferris Glovsky and Popeo, P.C.

(57) ABSTRACT

Described are implantable therapeutic devices, systems and methods to treat a patient. The device includes a hollow refillable housing for implantation within the posterior segment of an eye through a penetration in the sclera including a proximal retention structure protruding outward from a proximal end region of the housing, an access portion opening, and a penetrable barrier positioned at least in part within the access portion opening, the penetrable barrier configured to be repeatedly penetrated. A rigid porous structure is positioned within a region of the housing away from the access portion opening into a reservoir chamber extends along an axis between the penetrable barrier and the porous structure includes a volume sized to deliver therapeutic amounts of a therapeutic agent to the eye for an extended period of time. A cover is coupled to at least an upper surface of the proximal retention structure.

20 Claims, 9 Drawing Sheets

Related U.S. Application Data continuation of application No. 15/386,586, filed on Dec. 21, 2016, now Pat. No. 10,398,593, which is a continuation of application No. 14/228,130, filed on Mar. 27, 2014, now Pat. No. 9,526,654.

(60) Provisional application No. 61/806,267, filed on Mar. 28, 2013.

(56) References Cited

U.S. PATENT DOCUMENTS

| | | |
|---|---|---|
| 2,886,497 A | 5/1959 | Butler |
| 3,232,117 A | 2/1966 | Gilmont |
| 3,416,530 A | 12/1968 | Ness |
| 3,618,604 A | 11/1971 | Ness |
| 3,641,237 A | 2/1972 | Gould et al. |
| 3,826,258 A | 7/1974 | Abraham |
| 3,828,777 A | 8/1974 | Ness |
| 3,831,583 A | 8/1974 | Edmunds, Jr. et al. |
| 3,845,201 A | 10/1974 | Haddad et al. |
| 3,902,495 A | 9/1975 | Weiss et al. |
| 3,914,402 A | 10/1975 | Shel |
| 3,916,899 A | 11/1975 | Theeuwes et al. |
| 3,926,188 A | 12/1975 | Baker et al. |
| 3,949,748 A | 4/1976 | Malmin |
| 3,949,750 A | 4/1976 | Freeman |
| 3,961,628 A | 6/1976 | Arnold |
| 3,977,404 A | 8/1976 | Theeuwes |
| 3,986,510 A | 10/1976 | Higuchi et al. |
| 3,995,635 A | 12/1976 | Higuchi et al. |
| 4,008,719 A | 2/1977 | Theeuwes et al. |
| 4,014,333 A | 3/1977 | McIntyre |
| 4,014,334 A | 3/1977 | Theeuwes et al. |
| 4,014,335 A | 3/1977 | Arnold |
| 4,034,756 A | 7/1977 | Higuchi et al. |
| 4,034,758 A | 7/1977 | Theeuwes |
| 4,057,619 A | 11/1977 | Higuchi et al. |
| 4,077,407 A | 3/1978 | Theeuwes et al. |
| 4,111,201 A | 9/1978 | Theeuwes |
| 4,111,203 A | 9/1978 | Theeuwes |
| 4,135,514 A | 1/1979 | Zaffaroni et al. |
| 4,160,452 A | 7/1979 | Theeuwes |
| 4,164,559 A | 8/1979 | Miyata et al. |
| 4,179,497 A | 12/1979 | Cohen et al. |
| 4,186,184 A | 1/1980 | Zaffaroni |
| 4,200,098 A | 4/1980 | Ayer et al. |
| 4,220,152 A | 9/1980 | Dresback |
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,343,787 A | 8/1982 | Katz |
| 4,439,196 A | 3/1984 | Higuchi |
| 4,439,198 A | 3/1984 | Brightman, II et al. |
| 4,475,916 A | 10/1984 | Himmelstein |
| 4,484,922 A | 11/1984 | Rosenwald |
| 4,519,801 A | 5/1985 | Edgren |
| 4,609,374 A | 9/1986 | Ayer |
| 4,627,850 A | 12/1986 | Deters et al. |
| 4,634,418 A | 1/1987 | Binder |
| 4,634,427 A | 1/1987 | Hannula et al. |
| 4,673,405 A | 6/1987 | Guittard et al. |
| 4,693,886 A | 9/1987 | Ayer |
| 4,710,167 A | 12/1987 | Lazorthes |
| 4,712,550 A | 12/1987 | Sinnett |
| 4,730,013 A | 3/1988 | Bondi et al. |
| 4,737,150 A | 4/1988 | Baeumle et al. |
| 4,774,091 A | 9/1988 | Yamahira et al. |
| 4,777,049 A | 10/1988 | Magruder et al. |
| 4,781,675 A | 11/1988 | White |
| 4,781,680 A | 11/1988 | Redmond et al. |
| 4,840,615 A | 6/1989 | Hancock et al. |
| 4,851,228 A | 7/1989 | Zentner et al. |
| 4,853,229 A | 8/1989 | Theeuwes |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 4,979,938 A | 12/1990 | Stephen et al. |
| 5,049,142 A | 9/1991 | Herrick et al. |
| 5,053,030 A | 10/1991 | Herrick et al. |
| 5,084,021 A | 1/1992 | Baldwin |
| 5,092,837 A | 3/1992 | Ritch et al. |
| 5,098,443 A | 3/1992 | Parel et al. |
| 5,128,145 A | 7/1992 | Edgren et al. |
| 5,141,748 A | 8/1992 | Rizzo |
| 5,147,647 A | 9/1992 | Darougar |
| 5,164,188 A | 11/1992 | Wong |
| 5,171,270 A | 12/1992 | Herrick |
| 5,174,999 A | 12/1992 | Magruder et al. |
| 5,213,576 A | 5/1993 | Abiuso et al. |
| 5,238,687 A | 8/1993 | Magruder et al. |
| 5,277,912 A | 1/1994 | Lowe et al. |
| 5,282,829 A | 2/1994 | Hermes |
| 5,300,114 A | 4/1994 | Gwon et al. |
| 5,322,691 A | 6/1994 | Darougar et al. |
| 5,334,189 A | 8/1994 | Wade |
| 5,336,175 A | 8/1994 | Mames |
| 5,378,475 A | 1/1995 | Smith et al. |
| 5,413,572 A | 5/1995 | Wong et al. |
| 5,443,505 A | 8/1995 | Wong et al. |
| 5,466,233 A | 11/1995 | Weiner et al. |
| 5,476,511 A | 12/1995 | Gwon et al. |
| 5,516,522 A | 5/1996 | Peyman et al. |
| 5,554,132 A | 9/1996 | Straits et al. |
| 5,562,915 A | 10/1996 | Lowe et al. |
| 5,576,480 A | 11/1996 | Hopkins et al. |
| 5,578,042 A | 11/1996 | Cumming |
| 5,681,572 A | 10/1997 | Seare, Jr. |
| 5,702,414 A | 12/1997 | Richter et al. |
| 5,704,915 A | 1/1998 | Melsky et al. |
| 5,725,493 A | 3/1998 | Avery et al. |
| 5,766,151 A | 6/1998 | Valley et al. |
| 5,766,242 A | 6/1998 | Wong et al. |
| 5,770,076 A | 6/1998 | Chu et al. |
| 5,773,019 A | 6/1998 | Ashton et al. |
| 5,797,898 A | 8/1998 | Santini, Jr. et al. |
| 5,807,581 A | 9/1998 | Rosenblatt et al. |
| 5,824,072 A | 10/1998 | Wong |
| 5,830,173 A | 11/1998 | Avery et al. |
| 5,830,492 A | 11/1998 | Usala |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,904,144 A | 5/1999 | Hammang et al. |
| 5,916,584 A | 6/1999 | O'Donoghue et al. |
| 5,928,662 A | 7/1999 | Phillips |
| 5,951,512 A | 9/1999 | Dalton |
| 5,968,008 A | 10/1999 | Grams |
| 5,972,369 A | 10/1999 | Roorda et al. |
| 5,985,328 A | 11/1999 | Chu et al. |
| 5,989,216 A | 11/1999 | Johnson et al. |
| 5,993,414 A | 11/1999 | Haller |
| 6,001,386 A | 12/1999 | Ashton et al. |
| 6,096,070 A | 8/2000 | Ragheb et al. |
| 6,123,861 A | 9/2000 | Santini, Jr. et al. |
| 6,183,461 B1 | 2/2001 | Matsuura et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,306,426 B1 | 10/2001 | Olejnik et al. |
| 6,331,313 B1 | 12/2001 | Wong et al. |
| 6,331,523 B1 | 12/2001 | Kljavin et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,472,162 B1 | 10/2002 | Coelho et al. |
| 6,551,291 B1 | 4/2003 | de Juan, Jr. et al. |

(56) References Cited

U.S. PATENT DOCUMENTS

| | | |
|---|---|---|
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,083,803 B2 | 8/2006 | Peyman |
| 7,087,237 B2 | 8/2006 | Peyman |
| 7,090,681 B2 | 8/2006 | Weber et al. |
| 7,094,222 B1 | 8/2006 | Siekas et al. |
| 7,094,226 B2 | 8/2006 | Yaacobi |
| 7,117,870 B2 | 10/2006 | Prescott |
| 7,141,023 B2 | 11/2006 | Diermann et al. |
| 7,141,152 B2 | 11/2006 | Le Febre |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,276,050 B2 | 10/2007 | Franklin |
| 7,384,648 B2 | 6/2008 | Olejnik et al. |
| 7,468,065 B2 | 12/2008 | Weber et al. |
| 7,476,510 B2 | 1/2009 | Kapur et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,708,711 B2 | 5/2010 | Tu et al. |
| 7,709,049 B2 | 5/2010 | Chappa |
| 7,883,717 B2 | 2/2011 | Varner et al. |
| 7,893,040 B2 | 2/2011 | Loftsson et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,973,068 B2 | 7/2011 | Demopulos et al. |
| 8,096,972 B2 | 1/2012 | Varner et al. |
| 8,231,608 B2 | 7/2012 | Pang et al. |
| 8,231,609 B2 | 7/2012 | Pang et al. |
| 8,304,524 B2 | 11/2012 | Bairstow et al. |
| 8,399,006 B2 | 3/2013 | de Juan, Jr. et al. |
| 8,439,865 B2 | 5/2013 | Lust et al. |
| 8,486,052 B2 | 7/2013 | Varner et al. |
| 8,623,395 B2 | 1/2014 | de Juan, Jr. et al. |
| 8,795,712 B2 | 8/2014 | de Juan, Jr. et al. |
| 8,808,727 B2 | 8/2014 | de Juan, Jr. et al. |
| 8,992,503 B2 | 3/2015 | Shekalim |
| 9,126,007 B2 | 9/2015 | Alpini et al. |
| 9,883,968 B2 | 2/2018 | Doud et al. |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0118649 A1 | 6/2003 | Gao et al. |
| 2003/0119177 A1 | 6/2003 | Gruber et al. |
| 2003/0120217 A1 | 6/2003 | Abergel |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0233067 A1 | 12/2003 | McIntosh et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0024371 A1 | 2/2004 | Plicchi et al. |
| 2004/0029832 A1 | 2/2004 | Zeldis |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0133154 A1 | 7/2004 | Flaherty et al. |
| 2004/0171997 A1 | 9/2004 | Wilson et al. |
| 2004/0199128 A1 | 10/2004 | Morris et al. |
| 2004/0208910 A1 | 10/2004 | Ashton et al. |
| 2004/0209359 A1 | 10/2004 | Yayon et al. |
| 2004/0230183 A1 | 11/2004 | Breegi et al. |
| 2004/0247487 A1 | 12/2004 | Commercon et al. |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1 | 6/2005 | Bene et al. |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0244472 A1 | 11/2005 | Hughes et al. |
| 2005/0255144 A1 | 11/2005 | Schultz |
| 2005/0256499 A1 | 11/2005 | Pettis et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0277864 A1 | 12/2005 | Haffner et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0020248 A1 | 1/2006 | Prescott |
| 2006/0020253 A1* | 1/2006 | Prescott ............ A61F 9/00772 604/500 |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0078359 A1 | 4/2007 | Luloh et al. |
| 2007/0088414 A1 | 4/2007 | Campbell et al. |
| 2007/0088432 A1 | 4/2007 | Solovay et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |
| 2007/0191863 A1 | 8/2007 | De Juan et al. |
| 2007/0197491 A1 | 8/2007 | Robin et al. |

(56) References Cited

U.S. PATENT DOCUMENTS

| | | |
|---|---|---|
| 2007/0203174 A1 | 8/2007 | Klimko et al. |
| 2007/0212388 A1 | 9/2007 | Patravale et al. |
| 2007/0212397 A1 | 9/2007 | Roth |
| 2007/0219632 A1 | 9/2007 | Castillejos |
| 2007/0233037 A1 | 10/2007 | Gifford, et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0265599 A1 | 11/2007 | Castillejos |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0015545 A1 | 1/2008 | Sanchez et al. |
| 2008/0020045 A1 | 1/2008 | Chappa et al. |
| 2008/0027304 A1 | 1/2008 | Pardo et al. |
| 2008/0038316 A1 | 2/2008 | Wong et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0195218 A1 | 8/2008 | Jones |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0269318 A1 | 10/2008 | Romano |
| 2008/0286338 A1 | 11/2008 | Rosenthal et al. |
| 2008/0292679 A1 | 11/2008 | Lyons et al. |
| 2008/0293691 A1 | 11/2008 | Brigandi et al. |
| 2009/0005864 A1 | 1/2009 | Eggleston |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0061071 A1 | 3/2009 | McMorrow et al. |
| 2009/0074786 A1 | 3/2009 | Dor et al. |
| 2009/0081271 A1 | 3/2009 | Clarke et al. |
| 2009/0081272 A1 | 3/2009 | Clarke et al. |
| 2009/0082631 A1 | 3/2009 | Cronin et al. |
| 2009/0082863 A1 | 3/2009 | Schieber et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124986 A1 | 5/2009 | Hayakawa |
| 2009/0124997 A1 | 5/2009 | Pettis et al. |
| 2009/0192493 A1 | 7/2009 | Meng et al. |
| 2009/0196903 A1 | 8/2009 | Kliman |
| 2009/0214601 A1 | 8/2009 | Chappa et al. |
| 2009/0220572 A1 | 9/2009 | Deschatelets et al. |
| 2009/0224064 A1 | 9/2009 | Brodbeck et al. |
| 2009/0234449 A1 | 9/2009 | De Juan, Jr. et al. |
| 2009/0240208 A1 | 9/2009 | Cowan |
| 2009/0240215 A1 | 9/2009 | Humayun et al. |
| 2009/0247458 A1 | 10/2009 | Watson et al. |
| 2009/0258069 A1 | 10/2009 | Burnier et al. |
| 2009/0259212 A1 | 10/2009 | Sabbah |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0306025 A1 | 12/2009 | Lane |
| 2009/0306595 A1 | 12/2009 | Shih et al. |
| 2009/0318545 A1 | 12/2009 | Silver et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0075950 A1 | 3/2010 | Gant et al. |
| 2010/0083963 A1 | 4/2010 | Wharton et al. |
| 2010/0100043 A1 | 4/2010 | Racenet |
| 2010/0100054 A1 | 4/2010 | Cormier et al. |
| 2010/0114017 A1 | 5/2010 | Lenker et al. |
| 2010/0114309 A1 | 5/2010 | de Juan, Jr. et al. |
| 2010/0158980 A1 | 6/2010 | Kopczynski et al. |
| 2010/0168535 A1 | 7/2010 | Robinson et al. |
| 2010/0174272 A1* | 7/2010 | Weiner ............... A61F 9/0017 604/891.1 |
| 2010/0185205 A1 | 7/2010 | Novakovic et al. |
| 2010/0189765 A1 | 7/2010 | Erickson et al. |
| 2010/0197512 A1 | 8/2010 | Trinkle et al. |
| 2010/0216702 A1 | 8/2010 | Szkudlinski et al. |
| 2010/0221309 A1 | 9/2010 | Myers et al. |
| 2010/0223979 A1 | 9/2010 | Ploehn et al. |
| 2010/0255061 A1 | 10/2010 | de Juan, Jr. et al. |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0064740 A1 | 3/2011 | Burbidge et al. |
| 2011/0076278 A1 | 3/2011 | Khodadoust |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |
| 2011/0117083 A1 | 5/2011 | Bais et al. |

(56) References Cited

U.S. PATENT DOCUMENTS

| | | |
|---|---|---|
| 2011/0118677 A1* | 5/2011 | Wiley ............... A61M 39/0208 156/280 |
| 2011/0125178 A1 | 5/2011 | Drews et al. |
| 2011/0159073 A1 | 6/2011 | deJuan et al. |
| 2011/0190723 A1 | 8/2011 | Fangrow |
| 2011/0206646 A1 | 8/2011 | Alfonso et al. |
| 2011/0208122 A1 | 8/2011 | Shekalim |
| 2012/0028918 A1 | 2/2012 | Gupta |
| 2012/0029445 A1 | 2/2012 | de Juan, Jr. et al. |
| 2012/0029470 A1 | 2/2012 | Juan, Jr. et al. |
| 2012/0095439 A1 | 4/2012 | de Juan, Jr. et al. |
| 2012/0183799 A1 | 7/2012 | Steele et al. |
| 2012/0184905 A1 | 7/2012 | Shekalim |
| 2012/0209077 A1 | 8/2012 | Racenet |
| 2013/0116664 A1 | 5/2013 | Tai et al. |
| 2013/0204209 A1 | 8/2013 | de Juan, Jr. et al. |
| 2013/0218081 A1 | 8/2013 | Roth |
| 2013/0245544 A1 | 9/2013 | de Juan, Jr. et al. |
| 2013/0274691 A1 | 10/2013 | de Juan, Jr. et al. |
| 2013/0274692 A1 | 10/2013 | Alster et al. |
| 2013/0289482 A1 | 10/2013 | Meng et al. |
| 2013/0289497 A1 | 10/2013 | Humayun et al. |
| 2013/0296810 A1 | 11/2013 | Humayun et al. |
| 2013/0304031 A1 | 11/2013 | Varner et al. |
| 2013/0324918 A1 | 12/2013 | de Juan, Jr. et al. |
| 2013/0324942 A1 | 12/2013 | de Juan, Jr. et al. |
| 2014/0031769 A1 | 1/2014 | de Juan, Jr. et al. |
| 2014/0031833 A1 | 1/2014 | Novakovic et al. |
| 2014/0073714 A1 | 3/2014 | Reich et al. |
| 2014/0121609 A1 | 5/2014 | de Juan, Jr. et al. |
| 2014/0221941 A1 | 8/2014 | Erickson et al. |
| 2014/0243795 A1 | 8/2014 | Varner et al. |
| 2014/0276482 A1 | 9/2014 | Astafieva et al. |
| 2014/0328894 A1 | 11/2014 | de Juan, Jr. et al. |
| 2014/0336619 A1 | 11/2014 | Stankus et al. |
| 2014/0358125 A1 | 12/2014 | de Juan, Jr. et al. |
| 2015/0080846 A1 | 3/2015 | de Juan, Jr. et al. |
| 2015/0133896 A1 | 5/2015 | Benner et al. |
| 2015/0202079 A1 | 7/2015 | Shekalim |
| 2015/0224200 A1 | 8/2015 | de Juan, Jr. et al. |
| 2015/0231265 A1 | 8/2015 | Gupta |
| 2015/0250647 A1 | 9/2015 | de Juan, Jr. et al. |
| 2015/0282983 A1 | 10/2015 | Benner et al. |
| 2015/0297402 A1 | 10/2015 | de Juan, Jr. et al. |
| 2015/0351796 A1 | 12/2015 | Richard et al. |
| 2016/0038488 A1 | 2/2016 | Horvath et al. |
| 2016/0128867 A1 | 5/2016 | Bachelder et al. |
| 2016/0258855 A1 | 9/2016 | Farinas et al. |
| 2016/0270955 A1 | 9/2016 | Shekalim |
| 2016/0302965 A1 | 10/2016 | Erickson et al. |
| 2017/0165108 A1 | 6/2017 | Bianchi et al. |
| 2017/0165110 A1 | 6/2017 | Erickson et al. |
| 2017/0258634 A1 | 9/2017 | de Juan, Jr. et al. |
| 2018/0147204 A1 | 5/2018 | Horvath et al. |
| 2018/0161202 A1 | 6/2018 | de Juan, Jr. et al. |
| 2018/0243130 A1 | 8/2018 | Doud et al. |
| 2018/0243131 A1 | 8/2018 | Erickson et al. |
| 2018/0289542 A1 | 10/2018 | de Juan, Jr. et al. |
| 2018/0292403 A1 | 10/2018 | de Juan, Jr. et al. |
| 2019/0336335 A1 | 11/2019 | de Juan, Jr. et al. |

FOREIGN PATENT DOCUMENTS

| | | |
|---|---|---|
| CN | 1538826 A | 10/2004 |
| CN | 101052435 A | 10/2007 |
| CN | 101327356 A | 12/2008 |
| CN | 101600476 A | 12/2009 |
| CN | 101674824 A | 3/2010 |
| CN | 101754980 A | 6/2010 |
| CN | 101969897 A | 2/2011 |
| CN | 102365109 A | 2/2012 |
| CN | 102596097 A | 7/2012 |
| EP | 0033042 B1 | 8/1984 |
| EP | 0 228 185 A1 | 11/1986 |
| EP | 0498471 A2 | 8/1992 |
| EP | 0500143 A2 | 8/1992 |
| EP | 0671165 A2 | 9/1995 |
| EP | 0295248 B2 | 4/1999 |
| EP | 0944658 B1 | 6/2003 |
| EP | 1671624 | 6/2006 |
| EP | 1385452 B1 | 9/2006 |
| EP | 1409065 B1 | 1/2007 |
| EP | 1337284 B1 | 12/2007 |
| EP | 1911481 | 4/2008 |
| EP | 1521572 B1 | 3/2009 |
| JP | 01-149716 A | 6/1989 |
| JP | 01-197429 A | 8/1989 |
| JP | H 11507343 A | 6/1999 |
| JP | 2001-518880 A | 10/2001 |
| JP | 2004-516889 A | 6/2004 |
| JP | 2004-524866 A | 8/2004 |
| JP | 2005-500097 A | 1/2005 |
| JP | 2006-526430 A | 11/2006 |
| JP | 2008-500878 A | 1/2008 |
| JP | 2009-514888 A | 4/2009 |
| JP | 2009-523821 A | 6/2009 |
| JP | 2009-529968 A | 8/2009 |
| JP | 2010-521470 A | 6/2010 |
| JP | 2010526074 A | 7/2010 |
| RU | 2414199 C2 | 3/2011 |
| TW | 200500507 A | 1/2005 |
| WO | WO-88/04573 | 6/1988 |
| WO | WO-90/07545 | 7/1990 |
| WO | WO-95/28984 A1 | 11/1995 |
| WO | WO-97/29850 | 8/1997 |
| WO | WO-98/25982 | 6/1998 |
| WO | WO-98/43611 A1 | 10/1998 |
| WO | WO-99/11244 | 3/1999 |
| WO | WO-00/48660 | 8/2000 |
| WO | WO-01/26714 | 4/2001 |
| WO | WO-01/50943 | 7/2001 |
| WO | WO-01/68016 | 9/2001 |
| WO | WO-02/017831 A2 | 3/2002 |
| WO | WO-02/053128 A2 | 7/2002 |
| WO | WO-02/100318 | 12/2002 |
| WO | WO-03/028765 | 4/2003 |
| WO | WO-03/077972 | 9/2003 |
| WO | WO-03/082188 | 10/2003 |
| WO | WO-2004/000267 | 12/2003 |
| WO | WO-2004/073765 A2 | 9/2004 |
| WO | WO-2004/098565 A2 | 11/2004 |
| WO | WO-2004/112653 | 12/2004 |
| WO | WO-2005/016401 | 2/2005 |
| WO | WO-2005/027906 | 3/2005 |
| WO | WO-2005/028006 | 3/2005 |
| WO | WO-2005/091922 | 10/2005 |
| WO | WO-2005/107705 | 11/2005 |
| WO | WO-2005/110362 | 11/2005 |
| WO | WO-2005/110436 | 11/2005 |
| WO | WO-2005/110473 | 11/2005 |
| WO | WO-2005/117780 | 12/2005 |
| WO | WO-2006/014484 | 2/2006 |
| WO | WO-2006/015385 | 2/2006 |
| WO | WO-2006/023530 | 3/2006 |
| WO | WO-2006/031358 | 3/2006 |
| WO | WO-2006/031388 | 3/2006 |
| WO | WO-2006/044614 | 4/2006 |
| WO | WO-2006/050221 | 5/2006 |
| WO | WO-2006/068838 | 6/2006 |
| WO | WO-2006/071554 A2 | 7/2006 |
| WO | WO-2006/082588 A2 | 8/2006 |
| WO | WO-2006/108054 | 10/2006 |
| WO | WO-2006/125106 A1 | 11/2006 |
| WO | WO-2006/127962 | 11/2006 |
| WO | WO-2006/138609 | 12/2006 |
| WO | WO-2007/002184 A1 | 1/2007 |
| WO | WO-2007/012974 | 2/2007 |
| WO | WO-2007/035473 | 3/2007 |
| WO | WO-2007/035621 | 3/2007 |
| WO | WO-2007/038453 | 4/2007 |
| WO | WO-2007/044534 | 4/2007 |
| WO | WO-2007/047744 | 4/2007 |
| WO | WO-2007/056227 A2 | 5/2007 |

(56) References Cited

FOREIGN PATENT DOCUMENTS

| | | |
|---|---|---|
| WO | WO-2007/066339 | 6/2007 |
| WO | WO-2007/084582 | 7/2007 |
| WO | WO-2007/084765 | 7/2007 |
| WO | WO-2007/101204 | 9/2007 |
| WO | WO-2007/115259 A2 | 10/2007 |
| WO | WO-2007/117394 | 10/2007 |
| WO | WO-2007/131050 | 11/2007 |
| WO | WO-2007/133761 | 11/2007 |
| WO | WO-2007/133762 | 11/2007 |
| WO | WO-2008/003043 | 1/2008 |
| WO | WO-2008/005240 | 1/2008 |
| WO | WO-2008/011125 | 1/2008 |
| WO | WO-2008/019265 | 2/2008 |
| WO | WO-2008/033924 | 3/2008 |
| WO | WO-2008/040062 | 4/2008 |
| WO | WO-2008/045272 | 4/2008 |
| WO | WO-2008/052145 | 5/2008 |
| WO | WO-2008/060359 | 5/2008 |
| WO | WO-2008/061043 A2 | 5/2008 |
| WO | WO-2008/076544 | 6/2008 |
| WO | WO-2008/094989 | 8/2008 |
| WO | WO-2008/115290 | 9/2008 |
| WO | WO-2008/116165 | 9/2008 |
| WO | WO-2008/137236 A2 | 11/2008 |
| WO | WO-2008/144340 | 11/2008 |
| WO | WO-2008/144919 | 12/2008 |
| WO | WO-2008/147883 A1 | 12/2008 |
| WO | WO-2009/012075 | 1/2009 |
| WO | WO-2009/023615 | 2/2009 |
| WO | WO-2009/040336 A1 | 4/2009 |
| WO | WO-2009/046164 | 4/2009 |
| WO | WO-2009/055620 | 4/2009 |
| WO | WO-2009/055671 | 4/2009 |
| WO | WO-2009/055729 | 4/2009 |
| WO | WO-2009/055824 | 4/2009 |
| WO | WO-2009/061607 | 5/2009 |
| WO | WO-2009/073192 | 6/2009 |
| WO | WO-2009/086112 | 7/2009 |
| WO | WO-2009/089409 | 7/2009 |
| WO | WO-2009/094466 | 7/2009 |
| WO | WO-2009/112878 | 9/2009 |
| WO | WO-2009/117112 | 9/2009 |
| WO | WO-2009/124096 | 10/2009 |
| WO | WO-2009/128932 | 10/2009 |
| WO | WO-2009/134929 | 11/2009 |
| WO | WO-2009/137777 | 11/2009 |
| WO | WO-2010/008424 | 1/2010 |
| WO | WO-2010/021993 | 2/2010 |
| WO | WO-2010/047753 | 4/2010 |
| WO | WO-2010/062628 | 6/2010 |
| WO | WO-2010/066714 | 6/2010 |
| WO | WO-2010//075565 | 7/2010 |
| WO | WO-2010/078063 | 7/2010 |
| WO | WO-2010/088548 | 8/2010 |
| WO | WO-2010/093945 | 8/2010 |
| WO | WO-2010/095940 | 8/2010 |
| WO | WO-2010/096822 A2 | 8/2010 |
| WO | WO-2010/125416 | 11/2010 |
| WO | WO-2010/126908 | 11/2010 |
| WO | WO-2010/135369 | 11/2010 |
| WO | WO-2010/141729 | 12/2010 |
| WO | WO-2010/147661 | 12/2010 |
| WO | WO-2011/008896 | 1/2011 |
| WO | WO-2011/008897 | 1/2011 |
| WO | WO-2011/028850 | 3/2011 |
| WO | WO-2011/034627 | 3/2011 |
| WO | WO-2011/079232 | 6/2011 |
| WO | WO-2012/019047 A2 | 2/2012 |
| WO | WO-2012/019136 | 2/2012 |
| WO | WO-2012/065006 A2 | 5/2012 |
| WO | WO-2013/003620 | 1/2013 |
| WO | WO-2013/022801 | 2/2013 |
| WO | WO-2013/040247 A2 | 3/2013 |
| WO | WO-2014/150292 A1 | 9/2014 |
| WO | WO-2014/160884 A1 | 10/2014 |

OTHER PUBLICATIONS

AMD Preclinical Studies. Anti-Factor D Fab Specifically Inhibits the Alternative Pathway. The Association for Research in Vision and Ophthalmology, Inc. 2010. pp. 2984-2986.

Andrews, "Effect of nonsteroidal anti-inflammatory drugs on LFA-1 and ICAM-1 expression in gastric mucosa," Am J Physiol. Apr. 1994;266(4 Pt 1):G657-664.

ARVO, Agenda for the Summer Eye Research Conference, (Jul. 2009). 7 pages.

ASTM Designation: E 128-99. Standard Test Method for Maximum Pore Diameter and Permeability of Rigid Porous Filters for Laboratory Use. Aug. 1999. Retrieved Jul. 4, 2014. 3 pages.

Avery et al., "Intravitreal Bevacizumab (Avastin) for Neovascular Age-Related Macular Degeneration" Ophthalmology. Mar. 2006, vol. 113, No. 3:363-372.

Avery et al., "Intravitreal bevacizumab (Avastin) in the treatment of proliferative diabetic retinopathy," Ophthalmology. Oct. 2006, 113(10):1695-1705.e6.

Bakri et al., "The effect of intravitreal triamcinolone acetonide on intraocular pressure," Ophthalmic Surgery, Lasers and Imaging, Sep./Oct. 2003;34(5): 386-390.

Bird et al., Transport Phenomena, John Wiley & Sons, Inc., New York, 1960, pp. 196-201.

Block et al., "Solubility and dissolution of triamcinolone acetonide," Journal of Pharmaceutical Sciences, Apr. 1973; 62(4):617-621.

Breslin, C.W., et al., "Chapter 7. Slow Release Artificial Tears", *Symposium on Ocular Therapy* pp. 77-83, 1977.

Carbonaro, et al. "Nano-pore silicon membrane characterization by diffusion and electrical resistance." *Journal of Membrane Science.* 241 (2004):249-255.

Castro et al., "Effect of COX inhibitors on VEGF-induced retinal vascular leakage and experimental corneal and choroidal neovascularization," Exp Eye Res. Aug. 2004;79(2):275-285.

Chirila et al., "The Vitreous Humor" in *Handbook of Biomaterial Properties*, eds. Black & Hastings. Chapman & Hall, London, 1998; pp. 125-131.

Cousins et al., "Program # 1251—Targeting Complement Factor 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010. 2 pages.

Deissler et al., "VEGF-induced effects on proliferation, migration and tight junctions are restored by ranibizumab (Lucentis) in microvascular retinal endothelial cells," Br J Ophthalmol 2008;92:839-843.

Del Amo, et al., Current & future ophthalmic drug delivery systems . . . , *Drug Discovery Today*, vol. 13, Nos. 3/4, Feb. 2008. pp. 135-143.

Donoso et al., "The role of inflammation in the pathogenesis of age-related macular degeneration," Surv Ophthalmol. Mar.-Apr. 2006;51(2):137-52.

Duvvuri et al., Drug Delivery to the Retina: Challenges and Opportunities, *Expert Opinion on Biological Therapy*, 2003, vol. 3(1): 45-56.

European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.

Funatsu et al. "Association of vitreous inflammatory factors with diabetic macular edema," Ophthalmology 2009;116:73-79.

Gaudana et al., Recent Perspectives in Ocular Drug Delivery, *Pharmaceutical Research*, 2008. 20 pages.

Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.

Gillies et al., "Intravitreal triamcinolone for refractory diabetic macular edema: two-year results of a double-masked, placebo-controlled, randomized clinical trial," Ophthalmology. Sep. 2006;113(9):1533-1538.

(56) References Cited

OTHER PUBLICATIONS

Haller, An Overview of Sustained-release Drug Implants, Retinal Physician, Jan. 2008. 4 pages.

Hastedt & Wright, "Diffusion in porous materials above the percolation threshold," Pharm. Res. Sep. 1990; 7(9):893-901 (1990).

Heier et al, "Ketorolac versus prednisolone versus combination therapy in the treatment of acute pseudophakic cystoid macular edema," Ophthalmology. Nov. 2000;107(11):2034-2038;discussion 2039.

Janoria et al., Novel Approaches to Retinal Drug Delivery, *Expert Opinion Drug Delivery*, 2007. pp. 371-388.

Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface_area.pdf>>.

Jornitz et al. "Filter Integrity Testing in Liquid Applications, Revisited; Part 1." *Pharmaceutical Technology*. Oct. 2001. pp. 34-50.

Kang et al., "Inhibitory effects of anti-inflammatory drugs on interleukin-6 bioactivity," Biol Pharm Bull. Jun. 2001;24(6):701-703.

Katz, I.M., et al., "A Soluble Sustained-Release Ophthalmic Delivery Unit", 8:5 (May 1977) pp. 728-734.

Lamberts, D.W., M.D., et al., "A Clinical Study of Slow-Releasing Artificial Tears", *Ophthalmology* 85 (1978) pp. 794-800.

Lee, D.A., et al., "Glaucoma Filtration Surgery in Rabbits Using Bioerodible Polymers and 5-Fluorouracil", *Ophthalmology* 94:12 (1987) pp. 1523-1530.

Lee, D.A., et al., "The Use of Bioerodible Polymers and 5-Fluorouracil in Glaucoma Filtration Surgery", *Investigative Ophthalmology & Visual Science* 29-11 (1988) pp. 1692-1697.

Li, et al., An electrochemical introculardrug delivery device, *Science Direct, Sensors and Actuators*, www.sciencedirect.com, Jul. 4, 2007. pp. 41-48.

Lopez-Armada et al., "Modulation of cell recruitment by anti-inflammatory agents in antigen-induced arthritis," Ann Rheum Dis Nov. 2002;61(11):1027-1030.

Luncentis, INN-Ranibizumab, "Scientific Discussion," European Medicines Agency. Retrieved from the Internet:<http://www.ema.europa.eu/docs/en_GB/document_library/EPAR_Assessment_Report_-_Variation/human/000715/WC500101009.pdf>. Oct. 21, 2010. pp. 1-32.

Metal Powder Industries Federation, Porous Metal Design Guidebook, 2007, 24 pages total. Downloaded from the Internet: <<http://www.mpif.org/DesignCenter/porous.pdf>>.

Miller, DP, et al., Thermophysical Properties of Trehalose and Its Concentrated Aqueous Solutions,Pharmaceutical Research, vol. 14, No. 5, 1997, pp. 578-590.

Millipore. "Filter Integrity Test Methods." Millipore Corporation. 1999. 12 pages.

Molokhia et al, "Transscleral iontophoretic and intravitreal delivery of a macromolecule: Study of ocular distribution in vivo and postmortem with MRI", Experimental Eye Research 88 (2009) 418-425.

Moritera, T., et al., "Microspheres of Biodegradable Polymers as a Drug-Delivery System in the Vitreous", Investigative Ophthalmology & Visual Science 32-6 (1991) pp. 1785-1790.

MOTT Corporation, "Sintered Metal Powder Media," American Filtration & Separation Society 2007, 2 pages total. Downloaded from the Internet:<<http://www.afssociety.org/education/0907oneminute.htm>>.

Navarro, "The Optical Design of the Human Eye: a Critical Review," J Optom, Jan.-Mar. 2009 2(1): 3-18.

Nutan, MTH, et al., General Principles of Suspensions, in Pharmaceutical Suspensions From Formulation Development to Manufacturing, editors AK Kulshreshtha, et al., Spinger, 2010. pp. 39-65.

Okabe et al., "Intraocular tissue distribution of betamethasone after intrascleral administration using a non-biodegradable sustained drug delivery device," Investigative Ophthalmology and Visual Science. 2003;44:2702-2707. Downloaded from the Internet: <<http://www.iovs.org/cgi/reprint/44/6/2702>>.

Rosenfeld, "The Latest Research: Intravitreal Bevacizumab for Proliferative Diabetic Retinopathy," Review of Ophthalmology's Retina Online, Feb. 2006; retrieved from the Internet: http://www.revophth.com/archive/newsletter/0206_retina.htm. 2 pages.

Saline (medicine)—Wikipedia, the free encyclopedia. http://web.archive.org/web/20110205192937/http://en.wikipedia.org/wiki/Saline (medicine). Apr. 27, 2012. 4 pages.

Sanborn G.E., et al., Sustained-Release Ganciclovir Therapy for Treatment of Cytomegalovirus Retinitis, Use of an Intravitreal Device, Arch. Ophthalmol, vol. 110, 188-195 (Feb. 1992).

Sheardown and Saltzman, Novel Drug Delivery Systems for Posterior Segment Ocular Disease, Opthalmology: Ocular Angiogenesis: Diseases, Mechanisms and Therapeutics, 2007, pp. 393-408.

Smith et al., "Spectrophotometric determination of pKa values for fluorescein using activity coefficient corrections," WaterSA 2002; 28(4):395-402.

Smith, T.J., et al., "Intravitreal Sustained-Release Ganciclovir", Arch. Ophthamol 110 (1992) pp. 255-258.

Soheilian et al., "Pilot Study of Intravitreal Injection of Diclofenac for Treatment of Macular Edema of Various Etiologies," Retina, Mar. 2010; 30(3): 509-515.

Stay et al. Computer Simulation of Convective and Diffusive Transport of Controlled-Release Drugs in the vitreous Humor, Pharm Res 2003,20(1), pp. 96-102.

Theodossiadis et al., "Intravitreal administration of the anti-tumor necrosis factor agent infliximab for neovascular age-related macular degeneration," Am J Ophthalmol. May 2009;147(5):825-830.

Weiner, A.L., "Chapter 13: Polymeric Drug Delivery Systems for the Eye", *Polymeric Site-Specific Pharmacotherapy*, pp. 315-346, Edited by A.J. Domb (1994) John Wiley & Sons Ltd.

Williams et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.

Wright, P., et al. "Slow-Release Artificial Tear Inserts in the Treatment of Dry Eyes Resulting from the Oculomucocutaneous Syndrome", *British Journal of Ophthalmology* 67 (1983). pp. 393-397.

Yao et al. (Prevention of Laser Photocoagulation Induced Choroidal Neovascularization Lesions by Intravitreal Doses of Ranibizumab in Cynomolgus Monkeys, ARVO 2009 abstract D906). 2 pages.

* cited by examiner

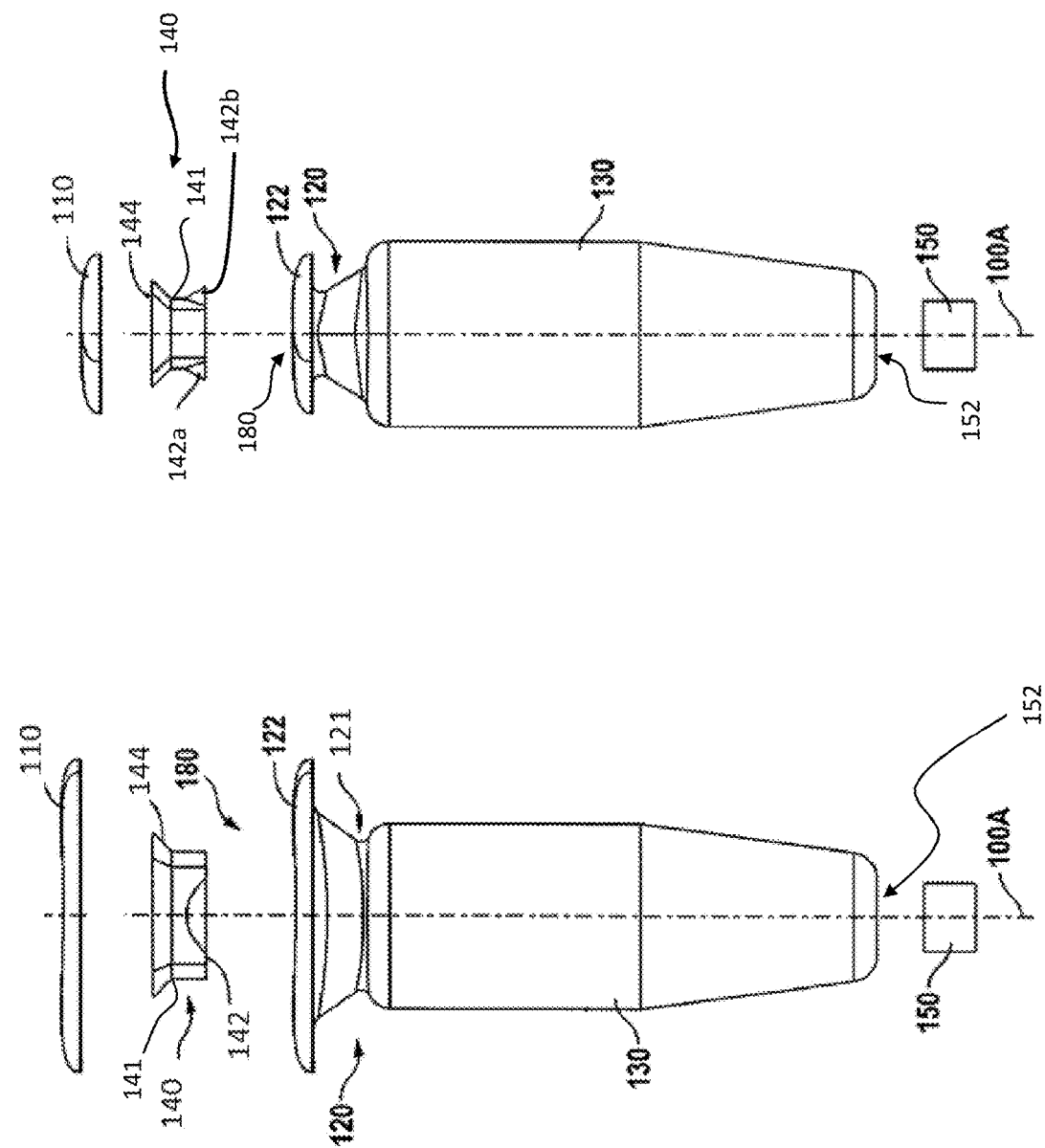

OPHTHALMIC IMPLANT FOR DELIVERING THERAPEUTIC SUBSTANCES

CROSS-REFERENCE TO PRIORITY DOCUMENT

This application is a continuation of U.S. patent application Ser. No. 16/514,128 filed Jul. 17, 2019, which is a continuation of U.S. patent application Ser. No. 15/386,586 filed Dec. 21, 2016, now U.S. Pat. No. 10,398,593, which is a continuation of U.S. patent application Ser. No. 14/228,130, filed Mar. 27, 2014, now U.S. Pat. No. 9,526,654, which claims the benefit of priority of U.S. Provisional Patent Application Ser. No. 61/806,267, filed Mar. 28, 2013, the full disclosures of which are hereby fully incorporated by reference.

BACKGROUND

Diseases that affect vision can be treated with a variety of therapeutic agents, but the delivery of drugs to the eye continues to be challenging. Injections of therapeutic via the eye can be painful, involve some risk of infection, hemorrhage and retinal detachment. Depending on the frequency, intra-ocular injections can be time-consuming for both patient and physician. Consequently, in at least some instances the drug may be administered less often than the prescribed frequency resulting in sub-optimal treatment benefit. Further, bolus intra-ocular injections may not provide the ideal pharmacokinetics and pharmacodynamics. A bolus injection of drug into the vitreous humor of a patient can result in a peak drug concentration several times higher than the desired therapeutic amount and then before the patient is able to get the next injection drop to a drug concentration that is far below therapeutic effectiveness.

SUMMARY

In one aspect, disclosed is an implantable therapeutic device to treat a patient. The device includes a hollow refillable housing for implantation within the posterior segment of an eye through a penetration in the sclera of the eye. The housing has a proximal end region. A proximal retention structure protrudes outward from the proximal end region and has an access portion opening. A penetrable barrier is positioned at least in part within the access portion opening and is configured to be repeatedly penetrated. A rigid porous structure is positioned within a region of the housing away from the access portion opening. A reservoir chamber extends along an axis between the penetrable barrier and the porous structure. The reservoir chamber includes a volume sized to deliver therapeutic amounts of a therapeutic agent to the eye for an extended period of time. The access portion opening opens into the reservoir chamber. A cover is coupled to at least an upper surface of the proximal retention structure.

In some variations, one or more of the following can optionally be included in any feasible combination in the above methods, apparatus, devices, and systems.

The access portion opening can be over-molded by the cover. The cover can encapsulate and bond the proximal retention structure and an upper surface of the penetrable barrier can be positioned within the access portion opening. The cover can encapsulate and bond to at least an upper surface of the proximal retention structure. The cover can encapsulate and bond to a lower surface of the proximal retention structure. The cover can maintain a seal of the reservoir chamber volume. The cover and the proximal retention structure can have the same shape profile. The cover and the penetrable barrier can be penetrated during filling of the reservoir chamber. The cover and the penetrable barrier can be configured to reseal after penetration of the reservoir chamber. The proximal retention structure can include one or more through-holes. The penetrable barrier can be pre-molded and the cover can be over-molded. The penetrable barrier can be a soft, high strength material and the cover can be a high durometer material. The cover can be a translucent material. The device can further include an anchor positioned within the access portion opening and in contact with at least a portion of the penetrable barrier. The penetrable barrier can further include a distal region that is flared and positioned within a proximal end region of the reservoir chamber.

In an interrelated aspect, disclosed is an implantable therapeutic device to treat a patient having a hollow refillable housing for implantation within the posterior segment of an eye through a penetration in the sclera of the eye. The housing has a proximal end region. A proximal retention structure is protruding outward from the proximal end region and includes an access portion opening. A penetrable barrier is positioned at least in part within the access portion opening. The penetrable barrier is configured to be repeatedly penetrated. A rigid porous structure is positioned within a region of the housing away from the access portion opening. A reservoir chamber extends along an axis between the penetrable barrier and the porous structure. The reservoir chamber has a volume sized to deliver therapeutic amounts of a therapeutic agent to the eye for an extended period of time. The access portion opening opens into the reservoir chamber. An anchor is positioned within the access portion opening and in contact with at least a portion of the penetrable barrier.

In some variations, one or more of the following can optionally be included in any feasible combination in the above methods, apparatus, devices, and systems.

The penetrable barrier can be pre-molded with soft, high strength material. The anchor can be formed of a high durometer material that resists deformation. The penetrable barrier can be bonded to the anchor creating a single septum structure. The anchor can engage an undercut feature in the proximal end of housing. The penetrable barrier can apply radial compression to the anchor. The device can further include a cover covering an upper surface of the proximal retention structure. The device can further include a sealing element positioned within a proximal end region of the reservoir chamber and coupled to the penetrable barrier.

More details of the devices, systems and methods are set forth in the accompanying drawings and the description below. Other features and advantages will be apparent from the description and drawings

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIGS. 3B-3C are exploded, side views of the therapeutic device of FIG. 3A;

DETAILED DESCRIPTION

Described herein are implantable devices, systems and methods of use for the delivery of one or more therapeutics for the treatment of diseases. The devices and systems described herein can deliver therapeutics to select regions and structures of the body over a variety of periods of time.

The devices and systems described herein have improved penetrable access portions for the repeated injection and long-term treatment and implantation of the device. It should be appreciated that the penetrable access portions as described herein can be used with a number of various different implantable therapeutic devices including one or more of those devices described U.S. Pat. Nos. 8,399,006; 8,623,395; PCT Pat. Publication No. WO2012/019136; PCT Pat. Publication No. WO2012/019047; and PCT Pat. Publication No. WO 2012/065006; the entire disclosures of which are incorporated herein by reference thereto.

Eye Anatomy

Figure 1:
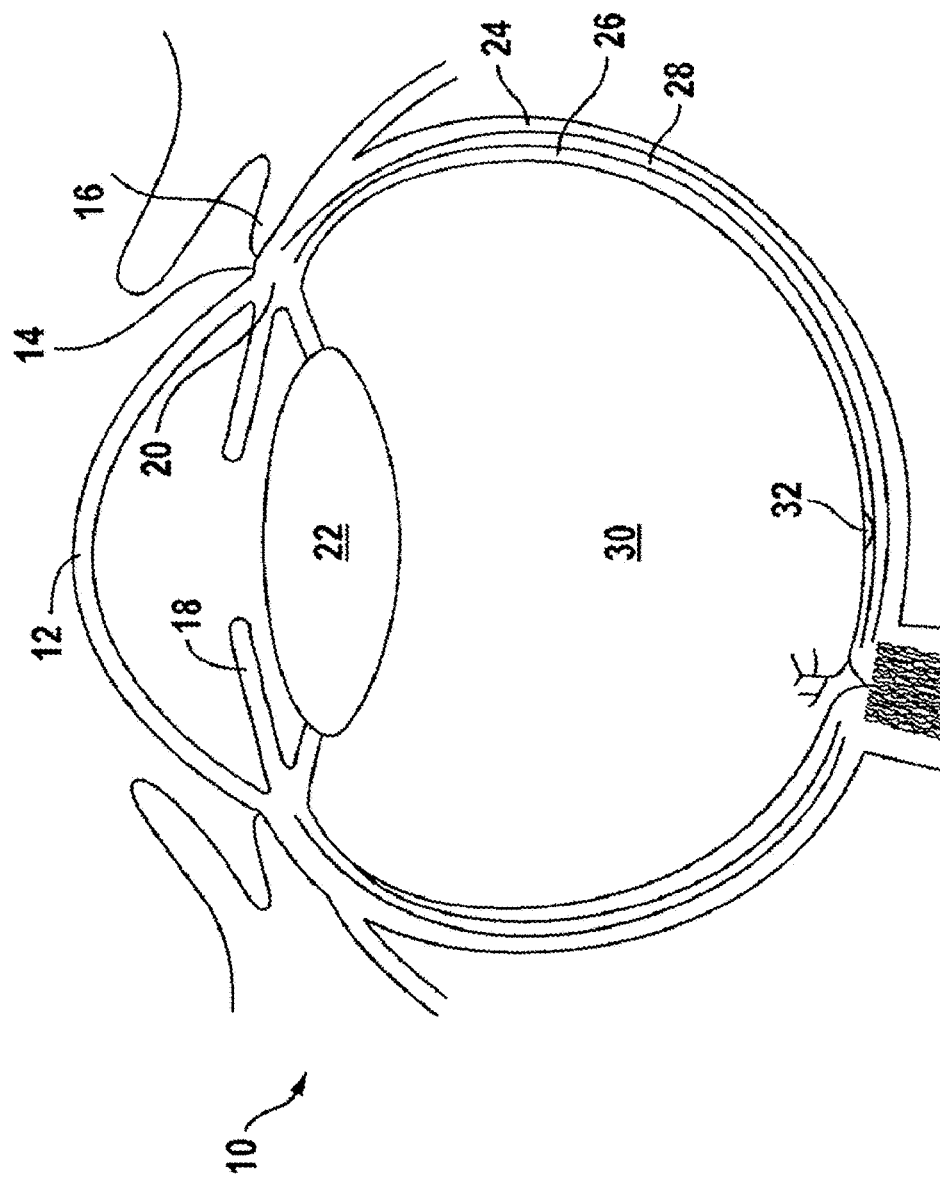
FIG. 1 is a cross-sectional, schematic view of a portion of the human eye.

FIG. 1 is a cross-sectional, schematic view of a portion of the human eye showing the anterior chamber, posterior chamber and vitreous body of the eye. The eye 10 is generally spherical and is covered on the outside by the sclera 24. The retina 26 lines the inside posterior segment of the eye 10 and includes the macula 32. The retina 26 registers the light and sends signals to the brain via the optic nerve. The bulk of the eye 10 is filled and supported by the vitreous body (vitreous humor) 30, a clear, jelly-like substance disposed between the lens 22 and the retina 26. The elastic lens 22 is located near the front of the eye 10. The lens 22 provides adjustment of focus and is suspended within a capsular bag from the ciliary body 20, which contains the muscles that change the focal length of the lens 22. A volume in front of the lens 22 is divided into two by the iris 18, which controls the aperture of the lens 22 and the amount of light striking the retina 26. The pupil is a hole in the center of the iris 18 through which light entering anteriorly passes. The volume between the iris 18 and the lens 22 is the posterior chamber. The volume between the iris 18 and the cornea 12 is the anterior chamber. Both chambers are filled with a clear liquid known as aqueous humor.

The cornea 12 extends to and connects with the sclera 24 at a location called the limbus 14 of the eye. The conjunctiva 16 of the eye is disposed over the sclera 24 and the Tenon's capsule (not shown) extends between the conjunctiva 16 and the sclera 24. The eye 10 also includes a vascular tissue layer called the choroid 28 that is disposed between a portion of the sclera 24 and the retina 26. The ciliary body 20 is continuous with the base of the iris 18 and is divided anatomically into pars plica and pars plana, a posterior flat area approximately 4 mm long. The pars plana region 25 is an example of a region of the eye suitable for placement and retention of the devices described herein. The eye 10 can include an insertion of the tendon of the superior rectus muscle to couple the sclera 24 of the eye to the superior rectus muscle. The devices described herein can be positioned in many locations of the pars plana region 25, for example away from tendon of the superior rectus muscle and one or more of posterior to the tendon, anterior to the tendon, under the tendon, or with nasal or temporal placement of the therapeutic device.

Figure 2:
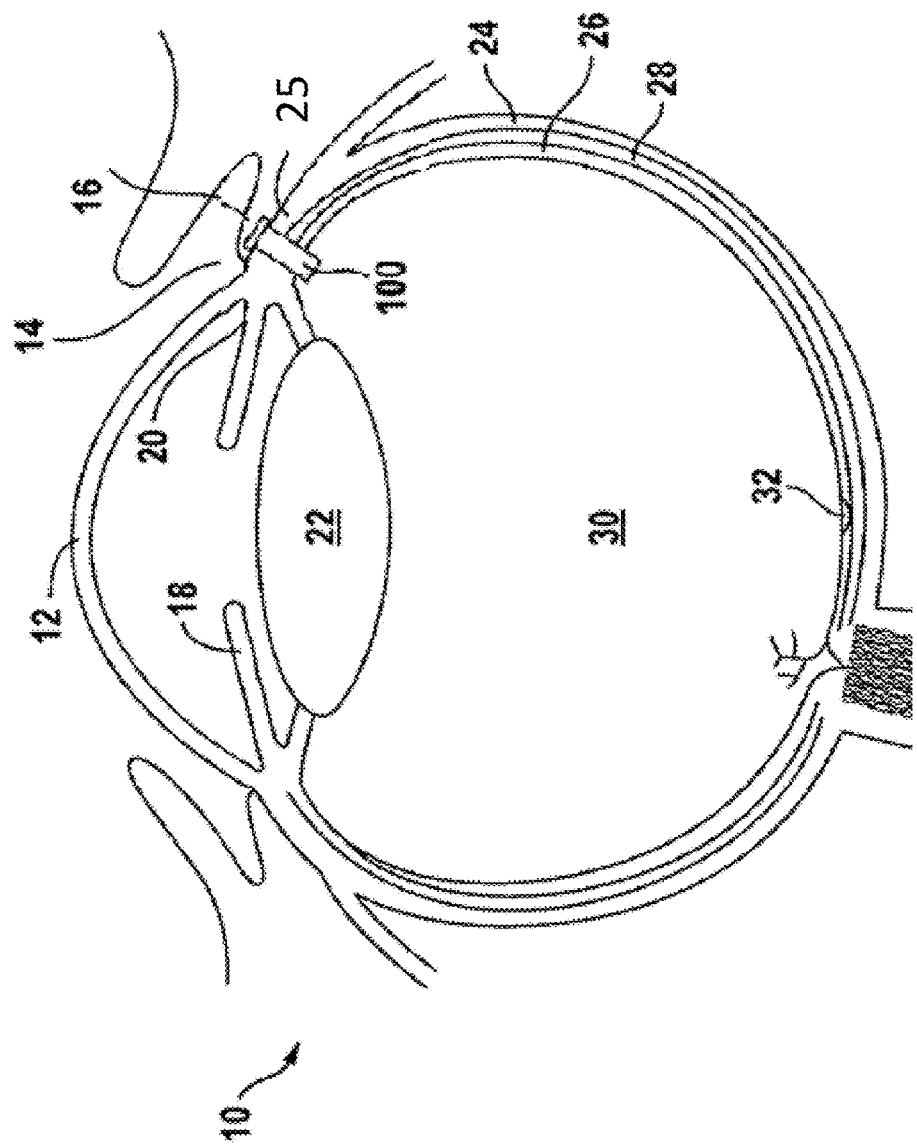
FIG. 2 is a cross-sectional, schematic view of a portion of the human eye having an implementation of a therapeutic device implanted therein.
Figure 3A:
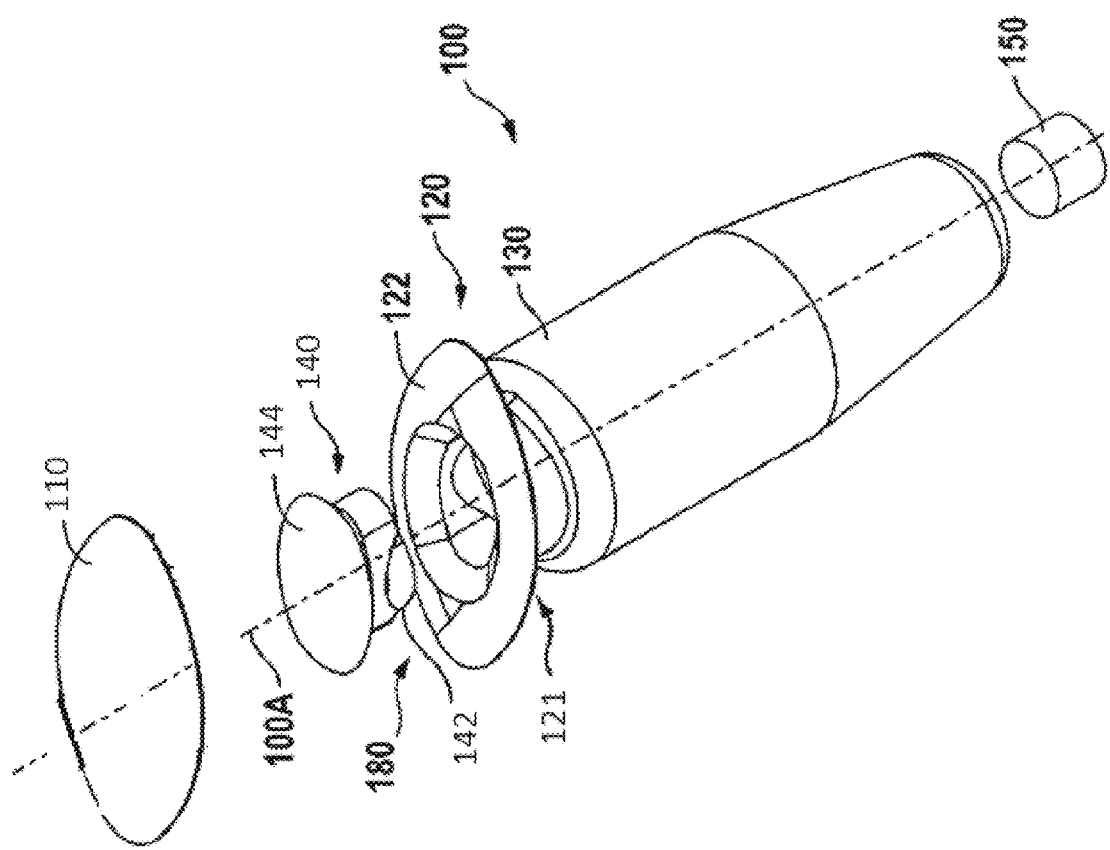
FIG. 3A is an exploded, perspective view of an implementation of a therapeutic device.
Figure 3D:
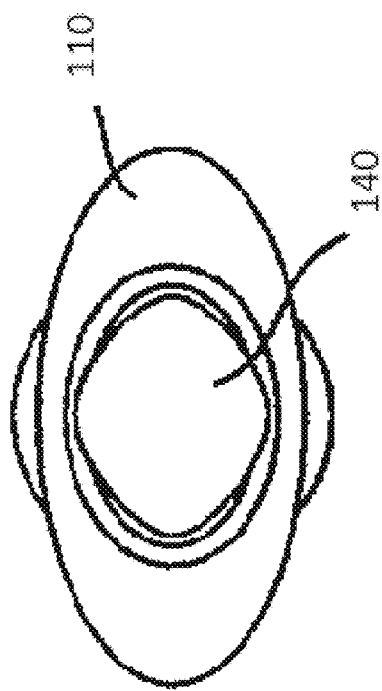
FIGS. 3D-3E are top and bottom views, respectively, of the therapeutic device of FIG. 3A.
Figure 3E:
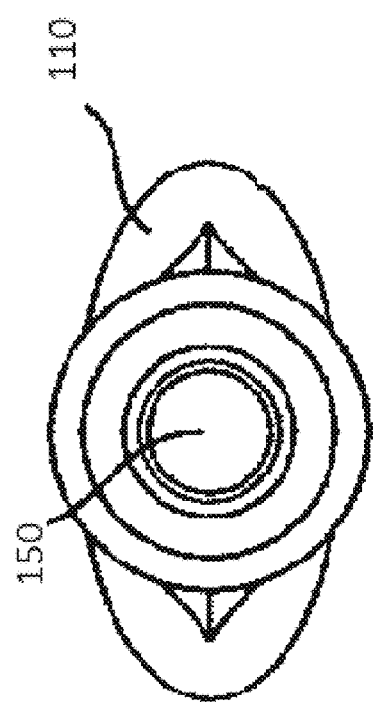
Figure 3F:
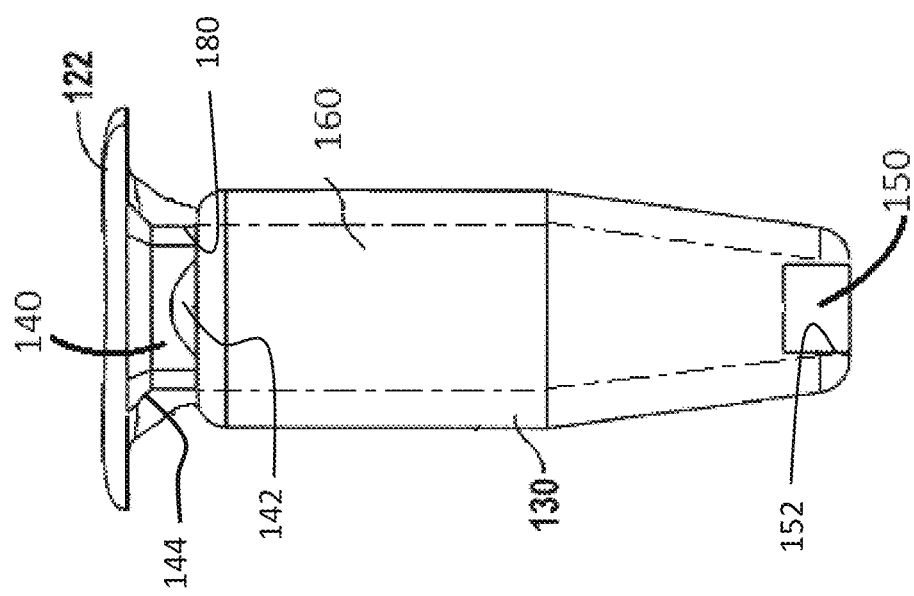
FIG. 3F is a side, cross-sectional view of the therapeutic device of FIG. 3A.

FIG. 2 shows an implementation of the therapeutic device 100 implanted at the pars plana region 25. The device 100 can be positioned so as to extend from the pars plana region 25 through the sclera 24 into the posterior segment of the eye including the vitreous body 30 so as to release the therapeutic agent into the vitreous body 30. The therapeutic device 100 can include a proximal, retention structure 120, such as a smooth protrusion at a proximal end region of the device 100, configured for placement along the sclera 24. In some implementations, the retention structure 120 can be positioned under the conjunctiva 16 such that the conjunctiva 16 can cover the therapeutic device and protect the therapeutic device 100. When the therapeutic agent is inserted or injected into the device 100, the conjunctiva 16 may be lifted away, incised, or punctured with a needle to access the therapeutic device 100.

It should be appreciated that the devices and systems described herein can be positioned in many locations of the eye and need not be implanted specifically as shown in the figures or as described herein. The devices and systems described herein can be used to deliver therapeutic agent(s) for an extended period of time to one or more of the following tissues: intraocular, intravascular, intraarticular, intrathecal, pericardial, intraluminal and intraperitoneal. Although specific reference is made below to the delivery of treatments to the eye, it also should be appreciated that medical conditions besides ocular conditions can be treated with the devices and systems described herein. For example, the devices and systems can deliver treatments for inflammation, infection, and cancerous growths. Any number of drug combinations can be delivered using any of the devices and systems described herein.

It should be appreciated that the devices and systems described herein can incorporate any of a variety of features described herein and that elements or features of one implementation of a device and system described herein can be incorporated alternatively or in combination with elements or features of another implementation of a device and system described herein as well as the various implants and features described in U.S. Pat. Nos. 8,399,006; 8,623,395; PCT Pat. Publication No. WO2012/019136; PCT Pat. Publication No. WO2012/019047; and PCT Pat. Publication No. WO 2012/065006. For example, the septum features described herein may be used with any of the various implementations of a device or system. For the sake of brevity, explicit descriptions of each of those combinations may be omitted although the various combinations are to be considered herein. Additionally, described herein are different methods for implantation and access of the devices. The various implants can be implanted, filled, refilled etc. according to a variety of different methods and using a variety of different devices and systems. Provided are some representative descriptions of how the various devices may be implanted and accessed, however, for the sake of brevity explicit descriptions of each method with respect to each implant or system may be omitted.

Implants

In a first implementation and as shown in FIGS. 3A-3F, the device 100 can include a housing 130, a penetrable barrier 140 and a porous structure 150. The housing 130 can be a rigid, hollow refillable housing for implantation within an interior chamber of the eye, such as the posterior segment of an eye through a penetration in the sclera of the eye. The housing 130 can have a proximal end region and a distal end region. The housing 130 can have an inner surface that defines, at least in part, a reservoir chamber 160 for holding a therapeutic material or agent(s) (see FIG. 3F). The penetrable barrier 140 can be positioned within a proximal end region of the housing 130 such as within an opening 180 in an access portion of the device that leads into a reservoir chamber 160 of the device. The porous structure 150 can be positioned within another region of the housing 130 a distance away from the penetrable barrier 140 such as within an opening 152 leading out of the reservoir chamber 160 of the device. For example, the porous structure 150 can be positioned near a distal end region of the housing 130 opposite the location of the more proximal penetrable barrier 140. The reservoir chamber 160 can have a volume sized to deliver therapeutic amounts of therapeutic agent to the eye for an extended period of time and the porous structure 150 can be configured to release therapeutic agent contained within the reservoir chamber 160 over the extended period of time. The housing 130 can include a retention structure 120 that can protrude outward from the proximal end region of the housing 130. The access portion opening 180 can be an opening in the device 100 that extends into the reservoir chamber 160. The penetrable barrier 140 can be positioned, at least in part, within the access portion opening 180 such that it forms a seal with the proximal end region of the housing 130. As will be described in more detail below, the devices described herein can also include a cover 110 coupled to at least a region of the device such as the retention structure 120. The cover 110 can cover, coat, cap, encapsulate, bond or otherwise couple to at least the penetrable barrier 140 of the device. The cover 110 can be configured to improve the integrity of the penetrable barrier 140 and its sealing engagement within the access portion opening 180 for repeated injection and long-term implantation.

Again with respect to FIGS. 3A-3F and as mentioned above, a distal end region of the housing 130 can include another opening 152, for example opposite the proximal access portion opening 180 into the reservoir chamber 160, that extends between the inside of the reservoir chamber 160 out of the housing 130. The porous structure 150 can be coupled to or positioned, at least in part, within the opening 152. It should be appreciated that the porous structure 150 can be coupled to or positioned within other regions besides the distal end region of the housing 130. The porous structure 150 can be affixed within an opening 152 in distal end of housing 130, for example with glue or other material(s). Alternatively or in combination, the distal end of the housing 130 can include an inner diameter sized to receive the porous structure 150, and the housing 130 can include a stop to position the porous structure 150 at a predetermined location on the distal end so as to define a predetermined size of reservoir chamber 160.

Still with respect to FIGS. 3A-3F, the reservoir chamber 160 within the housing 130 of the device 100 can extend along axis 100A between the penetrable barrier 140 positioned proximally within the access portion opening 180 to the location of the porous structure 150. Therapeutic formulations injected into device 100 can be released from the reservoir chamber 160 in accordance with the volume of the reservoir chamber 160 and a release characteristic or release rate index of the porous structure 150. The volume of the reservoir chamber 160 can be sized to deliver therapeutic amounts of a therapeutic agent to the eye for an extended period of time. The volume of the reservoir chamber 160 can be substantially determined by an inner cross sectional area of the housing 130, such as the distance between the proximal, penetrable barrier 140 and the porous structure 150. The release rate index (RRI) can be used to determine the release of the therapeutic from the device 100. RRI encompasses (PA/FL) where P comprises the porosity, A comprises an effective area, F comprises a curve fit parameter corresponding to an effective length and L comprises a length or thickness of the porous structure 150. Additional details regarding release characteristics of the porous structure 150 that can be used in the various devices described herein can be found, for example, in PCT Publication No. WO 2012/065006, which is incorporated herein by reference in its entirety.

The housing 130 can have a dimension such that its length generally exceeds its width or diameter. The housing 130 can have a diameter sized within a range, for example, from at least about 0.5 mm to at least about 4 mm, from at least about 1 mm to at least about 3 mm. In some implementations the diameter of the housing 130 at its widest point can be about 2 mm, for example. The housing 130 can have a length sized so as to extend from the conjunctiva 16 to the vitreous body 30 along axis 100A to release the therapeutic agent into the vitreous body 30. The housing 130 can have a length sized within a range, for example, from at least about 2 mm to at least about 14 mm, from at least about 4 mm to at least about 10 mm. In some implementations, the length of the housing 130 can be about 7 mm, for example. The above dimensions are provided as example dimensions and are not intended to be limiting. It should be appreciated that a variety and combination of dimensions are to be considered herein.

The housing 130 and reservoir chamber 160 can each (although not necessarily both) have an elliptical or oval cross-sectional shape, for example. This elongation of the device along one direction can allow for increased drug in the reservoir chamber 160 with a decrease interference in vision, for example, as the major axis of the ellipse can be aligned substantially with the circumference of the pars plana region 25 of the eye extending substantially around the cornea 12 of the eye, and the minor axis of the ellipse can be aligned radially with the eye so as to decrease interference with vision as the short axis of the ellipse extends toward the optical axis of the eye corresponding to the patient's line of sight through the pupil. Although reference is made to an elliptical or oval cross-section, many cross-sectional sizes and shapes can be used such as circular, square or rectangular with a short dimension extending toward the pupil of the eye and the long dimension extending along the pars plana of the eye.

One or more regions of the housing 130 of the devices described herein can be formed of a substantially rigid, biocompatible material. In some implementations, the walls of the housing 130 including at least the proximal retention structure 120 down to and including the porous structure 150 are substantially rigid such that the reservoir chamber 160 has a substantially constant volume when the therapeutic agent is released from the device so as to maintain a stable release rate profile, for example when the patient moves. The reservoir chamber 160 can remain substantially rigid and have a substantially constant volume even during injection of the therapeutic agent into the device, for example a device already implanted in the eye.

One or more regions of the housing 130, one or more regions of the retention structure 120 as well as other portions of the devices described herein, alone or in combination, can be formed of one or more of many biocompatible materials including, but not limited to materials such as acrylates, polymethylmethacrylate, siloxanes, metals, titanium stainless steel, polycarbonate, polyetheretherketone (PEEK), polyethylene, polyethylene terephthalate (PET), polyimide, polyimide-imide, polypropylene, polysulfone, polyurethane, polyvinylidene fluoride, polyphenylene polyphenylsulfone or PTFE, and others. Alternatively or in combination, one or more portions of the devices described herein, such as the housing 130, can be formed at least in part from an optically transmissive material such that the housing 130 can be translucent or transparent, such that when the device 100 is loaded with therapeutic agent the reservoir chamber 160 can be visualized outside the patient prior to implantation, for example when injected with a formulation of therapeutic agent prior to implantation in the physician's office. This visualization of the reservoir chamber 160 can be helpful to ensure that the reservoir chamber 160 is properly filled with therapeutic agent by the treating physician or assistant prior to implantation. For example, transparency can enable visualization, for example, using an indirect ophthalmoscope, of the contents of the reservoir chamber 160 of an implanted device allowing one to confirm that no air is trapped in the device and/or verify the clarity of the device contents. A cloudy appearance, for example, may indicate that some degree of contamination, microbial or otherwise, has occurred. The biocompatible, optically transmissive materials can include one or more of acrylate, polyacrylate, methlymethacraylate, polymethlymethacrylate (PMMA), polycarbonate, glass or siloxane.

The porous structure 150 can include one or more of a release control element, a release control mechanism, permeable membrane, a semi-permeable membrane, a material having at least one hole disposed therein, channels formed in a rigid material, straight channels, nano-channels, nano-channels etched in a rigid material, laser drilled holes, laser etched nano-channels, a capillary channel, a plurality of capillary channels, one or more tortuous channels, sintered material, sintered rigid material, sintered glass, sintered ceramic, sintered metal, sintered titanium, tortuous microchannels, sintered nano-particles, an open cell foam or a hydrogel such as an open cell hydrogel. Porous structures considered herein are described in U.S. Pat. Nos. 8,399,006; 8,623,395; PCT Publication No. WO2012/019136; PCT Publication No. WO2012/019047; and PCT Publication No. WO 2012/065006; the entire disclosures of which are incorporated herein by reference thereto.

Again with respect to FIGS. 3A-3F and as mentioned above, the retention structure 120 can protrude outward from the proximal end region of the housing 130. At least a first surface of the retention structure 120 can be configured to contact the sclera 24 and, in some implementations, can be configured to contact the conjunctiva 16 on at least a second surface of the retention structure 120. For example, at least a portion of the underside of the retention structure 120 can contact the sclera 24 and at least a portion of the upper side of the retention structure 120 can contact the conjunctiva 16. In some implementations, the retention structure 120 can be configured to contact the sclera 24 such that the retention structure 120 is at least partially embedded within the thickness of the sclera 24 and does not necessarily sit on an upper surface of the sclera or the conjunctiva.

The retention structure 120 can include a narrowed portion 121 and a wider, flanged portion 122 extending proximally from the narrowed portion 121. The narrowed portion 121 can have a cross-section sized to fit in an elongate incision or a puncture through the pars plana region 25 without causing gaping of the tissue near either end of the incision. For example, an incision can be made with a device having a straight, flat blade, for example a 3.2 mm blade. Penetrating the sclera with such a blade can result in exposed scleral tissue that may need to be sealed (e.g. 6.4 mm or 2×3.2 mm). A cross-sectional region of an implant positioned within the cut region of the sclera, for example having a perimeter of 6.4 mm and a diameter of about 2 mm, could open the wound such that there would be relatively large voids on either side of the device, for example about 2.2 mm between either side of the device and the farthest aspects of the exposed sclera. These voids can result in cut portions of the sclera remaining exposed and unsealed. The geometry of the narrowed portion 121 of the devices described herein can be designed to minimize the length of cut scleral tissue that remains exposed and/or unsealed.

The narrowed portion 121 can have a first cross-sectional distance across, or first dimensional width, and a second cross-sectional distance across, or second dimensional width, in which the first cross-sectional distance across is greater than the second cross-sectional distance across providing the narrowed portion 121 with an elongate cross-sectional profile. The elongate cross section of the narrowed portion 121 can be sized in many ways to fit the incision. The elongate cross section can have a first dimension longer than a second dimension and can have one or more of many shapes such as dilated slit, dilated slot, lentoid, oval, ovoid, or elliptical. It should also be appreciated that the narrowed portion 121 can have other cross sectional shapes, for example, a circular shape, if desired. The dilated slit shape and dilated slot shape can correspond to the shape assumed by the scleral tissue when cut and dilated. The lentoid shape can correspond to a biconvex lens shape. The elongate cross-section of the narrowed portion 121 can include a first curve along a first axis and a second curve along a second axis that is different than the first curve. The narrowed portion 121 can be sized and configured to receive the sclera 24 upon implantation in the eye 10 when the flanged portion 122 is positioned between the sclera 24 and the conjunctiva 16 and the distal end of the housing 130 extends into the vitreous body 30.

Flanged portion 122 of the retention structure 120 can include a first distance across and a second distance across. The first distance across can be greater than the second distance across (see FIGS. 3B and 3C, for example). The first distance across can result in the flanged portion 122 having a diameter greater than a largest diameter of the housing 130 (see e.g., FIG. 3B) whereas the second distance across can result in the flanged portion 122 having a diameter equal to or less than a largest diameter of the housing 130 (see e.g., FIG. 3C). The flanged portion 122 can have a variety of shapes, such as rectangular, square, oval, elliptical, circular, teardrop, polygonal or other shape. The flanged portion 122 can be formed as a smooth protrusion configured for placement along a portion of the sclera 24. In some implementations, the flanged portion 122 is positioned under the conjunctiva 16, such that the conjunctiva 16 covers and protects the device 100. The flanged portion 122 can be formed from a translucent material such that the physician can visualize tissue under the flanged portion 122 to assess the patient and to decrease appearance of the device 100 when implanted.

As mentioned above, the penetrable barrier 140 can be positioned, at least in part, within access portion opening 180 sealing the reservoir chamber 160 on a proximal end region of the device 100. The penetrable barrier 140 can be a septum configured to receive and be repeatedly penetrated by a sharp object such as a needle for injection of the therapeutic agent into the reservoir chamber 160. The penetrable barrier 140 can be configured to re-seal when the sharp object is removed. The penetrable barrier 140 can be a pre-molded soft, high strength material. In some implementations, the penetrable barrier 140 can be formed from one or more elastic materials such as siloxane, rubber, or another liquid injection molding silicone elastomer such as NUSIL MED-4810 (NuSil Silicone Technology, Carpinteria, CA). In some implementations, the penetrable barrier 140 can include an opaque material and/or a colored material such that it can be visualized by the treating physician.

Repeated injection as well as long-term implantation of the device 100 can affect the integrity of the penetrable barrier 140. For example, repeated injection through the penetrable barrier 140 can at least partially damage the device and negatively affect the seal between the inner surfaces of the housing 130, retention structure 120 and the outer surfaces of the penetrable barrier 140. Further, over time after implantation the penetrable barrier 140 can loosen relative to the housing 130. Described herein are features to improve the integrity of the penetrable barrier 140, its sealing engagement with the access portion opening 180 of the housing 130 and/or retention structure 120, and the effectiveness of the access region for repeated injection and long-term implantation of the re-fillable devices described herein.

As described above and as best shown in FIGS. 3A-3F, the penetrable barrier 140 can be positioned within a proximal end region of the housing 130 at least in part within an opening of the access portion 180. As such, the overall shape of the external surface of the penetrable barrier 140 can correspond generally to the shape of the surface(s) near the access portion opening 180 against which the penetrable barrier 140 contacts to mate and seal. It should be appreciated that the points of contact between the penetrable barrier 140 and the housing 130 can vary. The penetrable barrier 140 can make contact, for example sealing contact, with at least one or more surfaces or regions of the upper end of the reservoir chamber, the housing 130, the retention structure 120, the narrowed portion 121, the flanged portion 122, the access portion opening 180, and/or a combination thereof.

As best shown in FIGS. 3B-3C, the penetrable barrier 140 can have an upper region 144, a middle region 141, and a distal region 142. The upper region 144 can be sized to reside within and mate with at least a portion of the flanged portion 122. The upper region 144 can form an upper surface of the penetrable barrier 140 available through the access region opening 180 of the device. In some implementations, the outer surface of the upper region 144 can be beveled to correspond with the shape of and provide optimum mating engagement with an inner surface of the retention structure 120 that can also be beveled (see FIG. 3F). Engagement between the upper region 144 and the access portion opening 180 aids in forming a seal and retaining the penetrable barrier 140 within the access portion opening 180. The middle region 141 can be sized to reside within and mate with an inner surface of the narrowed portion 121 of the retention structure 120. As such, the middle region 141 can be a reduced diameter region or form a "waist" in the penetrable barrier 140. Alternatively, the middle region 141 can be relatively annular and have a generally planar outer surface configured to contact a corresponding planar surface forming the opening of the access region 180.

Figure 4B:
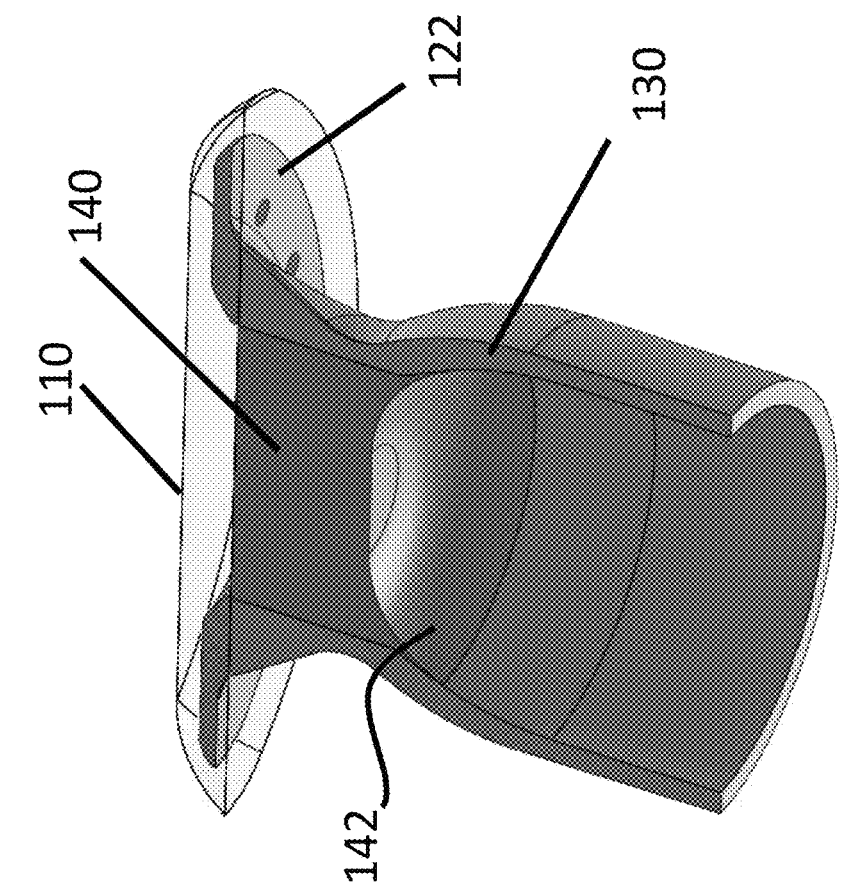
FIGS. 4A-4B are perspective and cross-sectional partial views, respectively, of an implementation of a therapeutic device.

In some implementations, the distal region 142 can have a diameter that is the same as or greater than the narrowed portion 121 of the retention structure 120 such that the distal region 142 helps to prevent withdrawal of the penetrable barrier 140 out of the access region 180. For example, the distal region 142 can have one or more tabs, a flared skirt, flange, rib or other feature of enlarged diameter compared to the middle and/or upper regions 141, 144 and sized to reside within and mate with at least a portion of the retention structure 120 located distal to the narrowed portion 121 and/or an upper region of the reservoir chamber 160 such as with an inner wall of the housing 130. In some implementations, the flange can have an upper surface configured to contact an inner wall surface near the upper end of the reservoir chamber 160 that surrounds the opening 180 of the access portion. The features of the distal region 142 having an enlarged diameter compared to the middle or upper regions 144, 141, such as the one or more tabs can also aid in forming a seal and retaining the penetrable barrier 140 within the access portion opening 180. For example, as best shown in FIG. 3C, the distal region 142 of the penetrable barrier 140 can include a first tab 142a positioned on a first region of the penetrable barrier 140 and a second tab 142b positioned on a second region of the penetrable barrier 140, such as a side opposite or a distance away from the first region. The tabs 142a, 142b can project away from the longitudinal axis 100A providing a cross-sectional diameter of the penetrable barrier 140 in at least one direction that is greater that the cross-sectional diameter of the middle region 141. The cross-sectional diameter of the penetrable barrier 140 distal to the middle region 141 in at least a first direction can be equal to, more or less than the cross-sectional diameter of the upper region 144. It should be appreciated that the distal region 142 can have one, two, three, four, or more tabs spaced around the wall of the penetrable barrier 140. It should also be appreciated that the entire distal region 142 of the penetrable barrier 140 can be flared away from the longitudinal axis 100A of the penetrable barrier 140 as shown in FIG. 4B to better engage an upper region of the housing 130 near the access region 180. In further implementations, the distal region 142 of the penetrable barrier 140 can be include a flange of an enlarged diameter. It should be appreciated that the distal region 142 as well as the entire penetrable barrier 140 itself can have a variety of shapes and features that act to improve retention within the upper end of the reservoir chamber 160. The features of one implementation of the penetrable barrier 140 can be used in combination or in the alternative with one or more implementations of the devices described herein.

The penetrable barrier 140 can be adhered within the device 100, for example, in at least a portion of the access portion opening 180 of the retention structure 120. Alternatively, the penetrable barrier 140 can be positioned into a proximal region of the device 100 in an adhesion-free manner and rely on the mating features between the external surface of the penetrable barrier 140 with the corresponding surfaces of the access portion opening 180 against which the penetrable barrier 140 abuts and seals.

As mentioned above, the devices described herein can be coupled to a cover 110 that can be configured to improve the integrity of the penetrable barrier 140 and its sealing engagement with the access portion opening 180 for repeated injection and long-term implantation. This provides a benefit to a device intended to be implanted long-term and re-filled while implanted, such as those described herein. The cover 110 can cap, coat, bond, encapsulate, cover, or otherwise couple to one or more components of the devices described herein. For example, at least a portion of a proximal end region of the device 100, including one or more combinations of the upper surface of the penetrable barrier 140 positioned within the opening of the access portion 180, an upper surface of the proximal retention structure 120 including the flanged portion 122, a lower surface of the proximal retention structure 120 including the flanged portion 122, the narrowed portion 121 of the retention structure 120, and at least a portion of an outer surface of the housing 130 near the proximal end region.

Figure 4A:
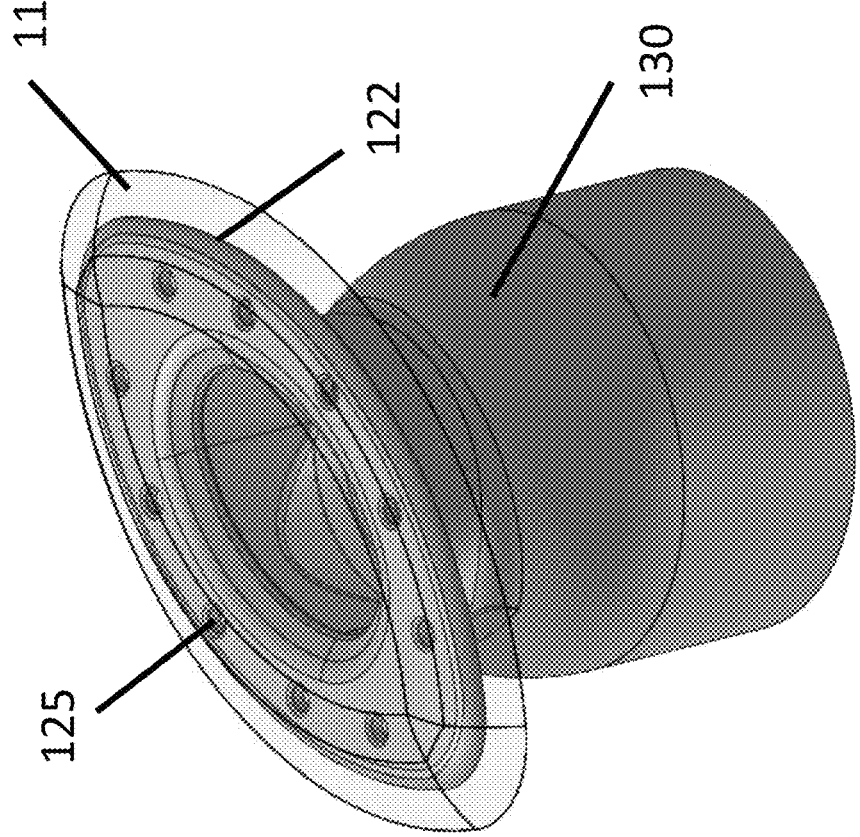

FIGS. 4A-4B show an implementation of a device in which the access portion opening 180, the penetrable barrier 140 and the retention structure 120 can be over-molded by the cover 110 such that the cover 110 can encapsulate and bond the access portion opening 180 and the upper surface of the penetrable barrier 140 positioned within the access portion opening 180. The cover 110 can encapsulate and bond to at least an upper surface of the proximal retention structure 120 as well as the lower surface of the proximal retention structure 120 (see, for example, FIG. 4B). The cover 110 can also encapsulate the flanged portion 122 such that the cover 110 bonds to at least the upper surface and also the lower surface of the flanged portion 122. The penetrable barrier 140 can be exposed or accessible on a proximal end region. The cover 110 can extend across the entire proximal end region of the device 100 such that it bonds to the flanged portion 122 and to the proximal end region of the penetrable barrier 140 positioned therein. As such, the cover 110 can supplement the bond between the penetrable barrier 140 and the inner surfaces of the device near the access portion opening 180 such as within the flanged region 120 and the inner surfaces of the proximal end region of the housing 130. The cover 110 can maintain or help to maintain a seal of the reservoir chamber volume. In some implementations, the cover 110 maintains the seal of the penetrable barrier 140 within the access portion opening 180 such that the seal of the reservoir chamber 160 need not rely on bonding between the surfaces of the housing 130 and the surfaces of the penetrable barrier 140. In some implementations, the cover 110 eliminates any need for a bond between the housing 130 and the penetrable barrier 140. Certain surface treatments can also be used during manufacturing of the devices described herein to enhance bonding between various components, including for example but not limited to, bonding primer agents such as NUSIL MED 161 or other surface activation techniques such as plasma treatment of the surfaces to be bonded.

The cover 110 and the proximal retention structure 120 (or any other region coupled to the cover 110 such as the flanged portion 122), can have corresponding shape profiles. The thickness of the over-molded cover 110 can vary from approximately 0.007" to approximately 0.025". The cover 110 can extend beyond the outer diameter of the flanged portion 122 as best shown in FIGS. 4A and 4B. The cover 110 can also extend upward from the upper surface of the flanged portion 122 and provide a slightly thicker and slightly higher profile to the access portion under the conjunctiva. During injection of the therapeutic agent into the reservoir chamber 160, the needle can extend through the cover 110 as it penetrates the barrier 140. The cover 110, like the penetrable barrier 140, can be configured to re-seal when the needle or other sharp object is withdrawn.

The proximal retention structure 120 can include one or more through-holes, apertures, indentations or other features. Again with respect to FIGS. 4A-4B, the flanged portion 122 can include one or more apertures 125 extending therethrough. Upon application of the cover 110, the apertures 125 can create mechanical struts of the over-molded cover material that extend through one or more regions of the flanged portion 122. The mechanical struts of over-molded cover material can provide some anchoring support as well as facilitating good filling of the over-mold. The apertures 125 can also allow for a thin, uniform layer of over-mold material to form on the underside of the flanged portion 122 or other another region of the retention structure during over-molding. It should be appreciated, however, that mechanical struts of the over-molded material can be formed by over-molded material extending only partially through apertures in the flanged portion 122. Further, instead of apertures 125, the flanged portion 122 can include only partial-thickness holes or indentations in the flanged portion 122. The indentations can be on an external surface of the flanged portion 122 such as in the upper and/or lower surfaces of the flanged portion 122. The external surfaces of the flanged portion 122 can also be textured such that the over-molded material of the cover 110 can penetrate and fill additional indented regions of the flanged portion 122 to provide a better coupling between the flanged portion 122 and the material of the cover 110.

The cover 110 can be an over-molded, high durometer material such as a translucent, liquid silicone rubber like MED-4880 or MED-4860 (NuSil Silicone Technology, Carpinteria, CA). The penetrable barrier 140 positioned within the proximal end region of the housing 130 can be a pre-molded soft, high strength material such as a liquid injection molding silicone elastomer such as MED-4810 (NuSil Silicone Technology, Carpinteria, CA).

Figure 5:
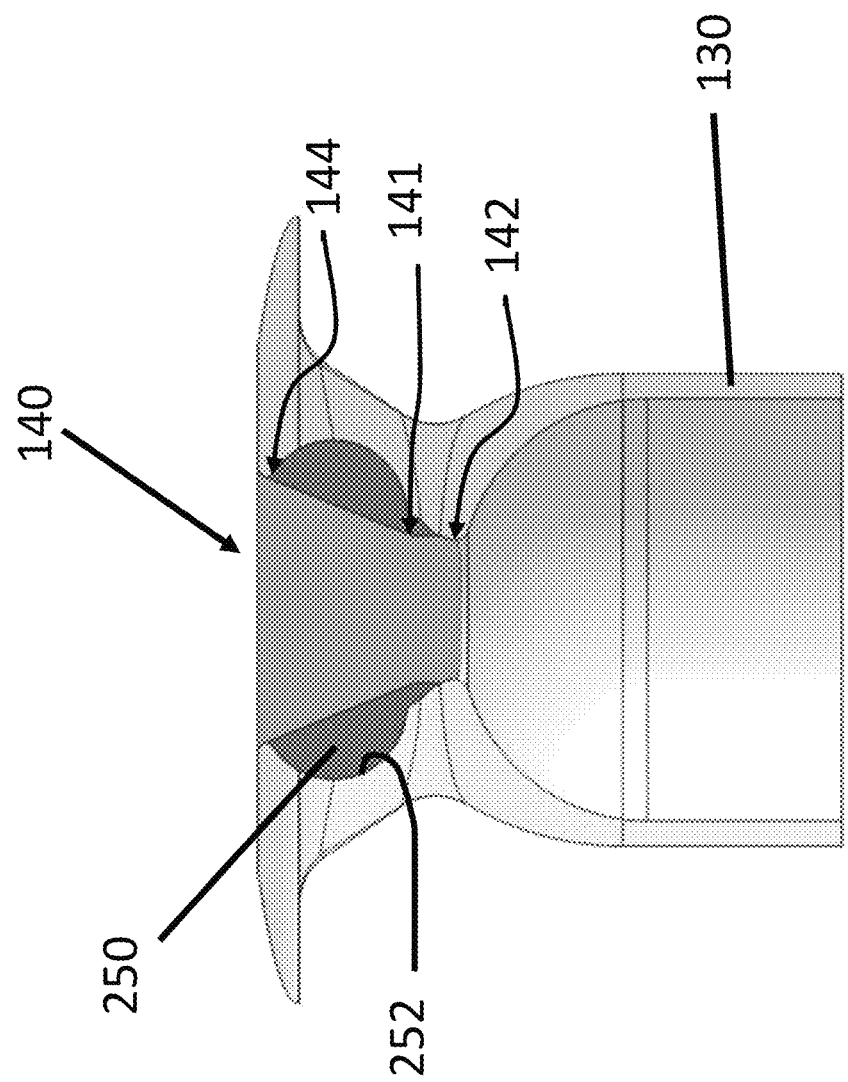
FIG. 5 is a side, cross-sectional partial view of an implementation of a therapeutic device.

FIG. 5 illustrates another implementation of a device that can include, alternatively or in combination with the cover 110, an anchor 250 to secure the septum structure within the access portion of the housing 130. The anchor 250 can provide further support to the penetrable barrier 140 as well as providing perimeter seal and added physical integrity useful during repeated penetration of the barrier 140 to refill the device. In some implementations, the anchor 250 can be an annular element encircling at least a portion of the penetrable barrier 140. An inner surface of the anchor 250 can contact and encircle at least a portion of the outer surface of the penetrable barrier 140. In some implementations, the anchor 250 encircles the upper region 144, the middle region 141, the distal region 142 or a combination of one or more of the upper, middle and distal regions of the penetrable barrier 140. The upper region 144 of the penetrable barrier 140 can be beveled such that the outer diameter of the upper region 144 is larger than the outer diameter of the middle region 141 of the penetrable barrier 140. Similarly, the shape of the inner surface of the anchor 250 can be beveled to match the shape of the outer surface of the penetrable barrier 140. Similarly, the inner surface of the anchor 250 can be shaped to match the outer surface of the distal region 142 of the penetrable barrier 140, which can be straight or flared or have one or more tabs or flanged regions as described above. Further, the outer surface of the anchor 250 can have a geometry that matches at least a portion of the geometry of the housing 130 at the access portion. For example, the outer surface of the 250 can engage with an undercut feature 252 in the proximal end of the housing 130. It should be appreciated that the anchor 250 can be, but is not necessarily, annular or ring-shaped. The anchor 250 can be any of a variety of shapes and can include one or more features that can be bonded to at least a region of the penetrable barrier. The outer surface of the anchor 250 can have any of a variety of shapes, including, but not limited to the rounded shape as shown in FIG. 5, curvilinear such as oval, circular, or elliptical, as well as being angular in shape such as triangular, rectangular, or other number of angles. The anchor 250 can have sufficient physical robustness so as to translate to a secure mechanical interference with internal aspects of the rigid, body device in the area of the penetrable barrier.

The penetrable barrier 140 can be pre-molded with a soft, high strength material such as a liquid injection molding silicone elastomer such as MED-4810 (NuSil Silicone Technology, Carpinteria, CA). The anchor 250 can be formed of a higher durometer material such as a translucent, liquid silicone rubber like MED-4880 (NuSil Silicone Technology, Carpinteria, CA). The pre-mold penetrable barrier 140 can be bonded to the annular anchor 250 creating a single septum structure for insertion within the proximal end of the housing 130. The pre-mold penetrable barrier 140 and anchor 250 can be bonded together within the housing 130 or can be bounded outside the device and loaded into positioned once a single septum structure is formed. The higher durometer of the anchor 250 can resist deformation and create a mechanical lock fixing the location of the septum in the housing 130. The pre-mold penetrable barrier 140 can apply radial compression to the outer anchor 250 and housing 130 to maintain septum seal performance. The radial compression of the penetrable barrier 140 can encourage re-sealing after penetration following filling or re-filling of the reservoir chamber, for example re-sealing of a needle track upon removal of the needle. The radial compression of the penetrable barrier 140 can be provided by the pre-mold penetrable barrier 140 being larger in dimension relative to the access portion of the housing 130 in which it is positioned and the access portion of the housing 130 being formed of a more rigid material than the softer, pre-mold penetrable barrier 140.

Figure 6:
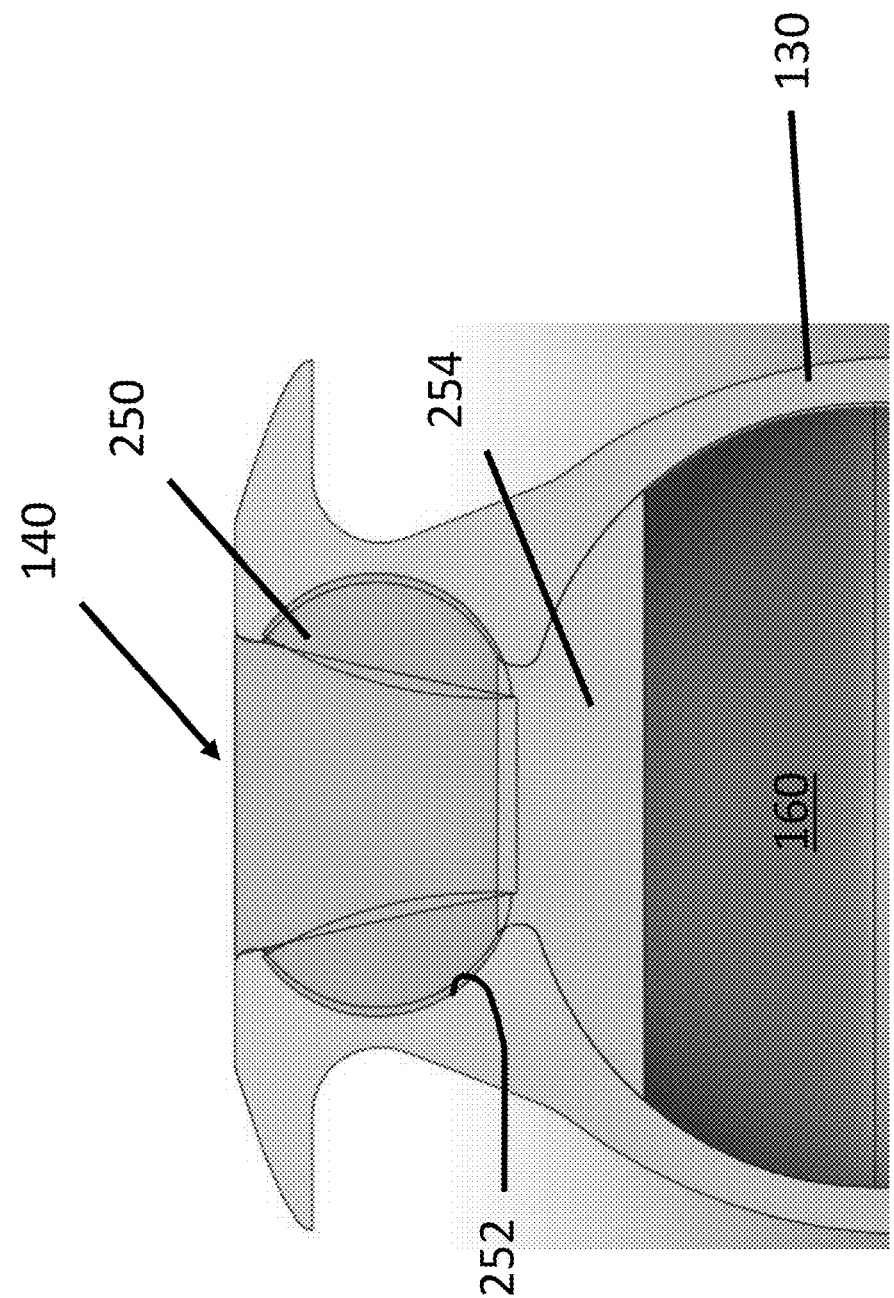
FIG. 6. is a side, cross-sectional partial view of an implementation of a therapeutic device.

FIG. 6 illustrates an interrelated implementation of a device that can include, alternatively or in combination with the cover 110, an anchor 250. As described above, the anchor 250 can secure the septum structure within the access portion opening 180 of the housing 130. The anchor 250 can provide further support to the penetrable barrier 140 as well as providing perimeter seal and added physical integrity. As with other implementations described herein, the anchor 250 can be an annular element encircling at least a portion of the penetrable barrier 140. An inner surface of the anchor 250 can contact and encircle at least a portion of the outer surface of the penetrable barrier 140. The inner surface of the anchor 250 can have a shape that corresponds to the outer surface of the penetrable barrier 140 and the outer surface of the anchor 250 can have a shape that corresponds to the inner surface of the access portion opening 180 of the housing 130, for example such that it engages an undercut feature 252 in the proximal end of the housing 130. The anchor 250 can be formed of a high durometer material to provide further support to the penetrable barrier 140 as well as providing perimeter seal and added physical integrity as described above. The penetrable barrier 140 can be a pre-molded, low durometer material also as described above. Further, the penetrable barrier 140 can be oversized such that the penetrable barrier 140 provides radial compression to the anchor 250 to provide improved needle track sealing as described above.

As described above, the penetrable barrier 140 can include a distal region 142 having a flared, flanged or otherwise enlarged diameter compared to the middle region 141 and/or upper region 144 of the penetrable barrier 140. The enlarged distal region 142 can be positioned within the access portion opening 180, for example, where the access portion opening 180 opens into the reservoir chamber 160 at a proximal end region of the reservoir chamber 160. As shown in FIG. 6, the penetrable barrier 140 can also include a sealing element 254 near its distal end region that is flared and/or creates a "skirt" within a proximal end region of the reservoir chamber 160. The sealing element 254 can be positioned in a proximal end of the reservoir chamber 160 of the housing 130 to provide a secondary seal and to prevent withdrawal of the penetrable barrier 140 in a proximal direction. It should be appreciated the sealing element 254 can be a separate element coupled to the penetrable barrier 140, for example to the distal region 142 of the penetrable barrier 140. Alternatively, the sealing element 254 can be integral with the penetrable barrier 140 such as the flared distal end region 142 shown in FIG. 4B. As such, the sealing element 254 can be a low durometer material that is the same as or different from the material of the penetrable barrier 140. It should also be appreciated that the variations described above, such as the cover 110 can also be incorporated with the implementation shown in FIG. 6. It should be appreciated that the one or more of the components described herein can optionally be included in any feasible combination with the various implementations described herein.

The housing 130 can be machined from a piece of material, or injection molded, so as to form the retention structure 120, flange 122 and/or the narrowed portion 121. As described above, the penetrable barrier 140 can be pre-molded and the cover 110 can be over-molded. Alternatively, the cover 110 can be pre-molded and bonded to the pre-molded penetrable barrier 140. The penetrable barrier 140 and cover 110 can be the same material and over-molded around the flange 122 using a single step injection molding process. Alternatively, the penetrable barrier 140 or cover 110 can be two different materials and over molded around the flange and cured in two independent steps. Further, the anchor 250 and/or sealing element 254 can be pre-molded and bonded to pre-molded penetrable barrier 140. The anchor 250 and/or sealing element 254 can be casted in the housing and the pre-penetrable barrier 140 can be compressed into the housing and bonded to the anchor 250 and/or sealing element 254. Alternatively, the sealing element 254 can be formed by a distal flared portion of the pre-molded penetrable barrier 140.

Therapeutics

Initial filling of the device 100 with one or more therapeutic agents can occur prior to insertion or after insertion in a patient's eye. The penetrable barrier 140 as well as the cover 110, if present, can be penetrated with a needle or access device attached to a syringe or injection device containing therapeutic agent. The cover 110 and the penetrable barrier 140 can be penetrated during filling and/or refilling of the reservoir chamber 160. The needle or access device can be inserted through the penetrable barrier 140 until a distal opening of the needle enters the reservoir chamber 160. The contents of the syringe or injection device can be injected into the reservoir chamber 160 and the needle or access device can be removed from the penetrable barrier 140. The cover 110 and the penetrable barrier 140 can be configured to reseal after penetration during filling and/or refilling of the reservoir chamber 160. The penetrable barrier 140 can reseal around the path created by the needle or access device upon its removal. The device 100 also can be periodically refilled with therapeutic agent following surgical placement as needed by accessing the implanted device 100 and without necessitating device removal. The conjunctiva 16 can be lifted or incised away. Alternatively, the conjunctiva can be pierced with the needle or access device used to fill the device 100 such that a single penetration is performed through each of the conjunctiva, cover 110 (if present), and penetrable barrier 140. Once the needle or access device is inserted and located at the appropriate depth within the reservoir chamber 160, injection of fresh therapeutic solution or exchange of pre-existing reservoir contents with fresh therapeutic solution can take place.

The therapeutic devices described herein can be implanted in the eye to treat the eye for as long as is helpful and beneficial to the patient. For example the device can be implanted for at least about 1 year, 2 years, 3 years, 4 year, 5 years and up to permanently for the life of the patient. Alternatively or in combination, the device can be removed when no longer helpful or beneficial for treatment of the patient. In other implementations, the device can be implanted for at least about 4 years to 10 years, for example a duration of treatment period for a chronic disease such as diabetic macular edema or age-related macular degeneration. The device can be periodically refilled in the physician's office with new therapeutic agent as indicated by disease progression. For diseases such as age-related macular degeneration, the device can be refilled as frequently as once every week, bi-weekly, monthly, bi-monthly, every 3 months, every 4 to 6 months, every 3 to 9 months, every 12 months, or any other period as indicated to treat a disease.

It should be appreciated that a variety of diseases and/or conditions can be treated with the devices and systems described herein, for example: glaucoma, macular degeneration, retinal disease, proliferative vitreoretinopathy, diabetic retinopathy, uveitis, keratitis, cytomegalovirus retinitis, cystoid macular edema, herpes simplex viral and adenoviral infections and other eye diseases, eye infections (including, but not limited to, infections of the skin, eyelids, conjunctivae, and/or lacrimal excretory system), orbital cellulitis, dacryoadenitis, hordeolum, blepharitis, conjunctivitis, keratitis, corneal infiltrates, ulcers, endophthalmitis, panophthalmitis, viral keratitis, fungal keratitis herpes zoster ophthalmicus, viral conjunctivitis, viral retinitis, uveitis, strabismus, retinal necrosis, retinal disease, vitreoretinopathy, diabetic retinopathy, cytomegalovirus retinitis, cystoids macular edema, herpes simplex viral and adenoviral injections, scleritis, mucormycosis, canaliculitis, acanthamoeba keratitis, toxoplasmosis, giardiasis, leishmanisis, malaria, helminth infection, etc. It also should be appreciated that medical conditions besides ocular conditions can be treated with the devices and systems described herein. For example, the devices can deliver drugs for the treatment of inflammation, infection, cancerous growth. It should also be appreciated that any number of drug combinations can be delivered using any of the devices and systems described herein.

The devices described herein can be used to deliver essentially any substance. As used herein, "substance," "drug" or "therapeutic" is an agent or agents that ameliorate the symptoms of a disease or disorder or ameliorate the disease or disorder including, for example, small molecule drugs, proteins, nucleic acids, polysaccharides, and biologics or combination thereof. Therapeutic agent, therapeutic compound, therapeutic regimen, or chemotherapeutic include conventional drugs and drug therapies, including vaccines, which are known to those skilled in the art. Therapeutic agents include, but are not limited to, moieties that inhibit cell growth or promote cell death, that can be activated to inhibit cell growth or promote cell death, or that activate another agent to inhibit cell growth or promote cell death. Optionally, the therapeutic agent can exhibit or manifest additional properties, such as, properties that permit its use as an imaging agent, as described elsewhere herein. Exemplary therapeutic agents include, for example, cytokines, growth factors, proteins, peptides or peptidomimetics, bioactive agents, photosensitizing agents, radionuclides, toxins, anti-metabolites, signaling modulators, anti-cancer antibiotics, anti-cancer antibodies, angiogenesis inhibitors, radiation therapy, chemotherapeutic compounds or a combination thereof. The drug may be any agent capable of providing a therapeutic benefit. In an embodiment, the drug is a known drug, or drug combination, effective for treating diseases and disorders of the eye. In non-limiting, exemplary embodiments, the drug is an antiinfective agent (e.g., an antibiotic or antifungal agent), an anesthetic agent, an anti-VEGF agent, an anti-inflammatory agent, a biological agent (such as RNA), an intraocular pressure reducing agent (i.e., a glaucoma drug), or a combination thereof. Non-limiting examples of drugs are provided below.

The therapeutic agent can include a macromolecule, for example an antibody or antibody fragment. The therapeutic macromolecule can include a VEGF inhibitor, for example commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™ Avastin™, Macugen™ and VEGF Trap. The therapeutic agent can include small molecules such as of a corticosteroid and analogues thereof. For example, the therapeutic corticosteroid can include one or more of trimacinalone, trimacinalone acetonide, dexamethasone, dexamethasone acetate, fluocinolone, fluocinolone acetate, or analogues thereof. Alternatively or in combination, the small molecules of therapeutic agent can include a tyrosine kinase inhibitor comprising one or more of axitinib, bosutinib, cediranib, dasatinib, erlotinib, gefitinib, imatinib, lapatinib, lestaurtinib, nilotinib, semaxanib, sunitinib, toceranib, vandetanib, or vatalanib, for example. The therapeutic agent can include an anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™), sorafenib (Nexavar™) axitinib, or pazopanib. The therapeutic agent can include a therapeutic agent suitable for treatment of dry AMD such as one or more of Sirolimus™ (Rapamycin), Copaxone™ (Glatiramer Acetate), Othera™, Complement C5aR blocker, Ciliary Neurotrophic Factor, Fenretinide or Rheopheresis. The therapeutic agent can include a therapeutic agent suitable for treatment of wet AMD such as one or more of REDD14NP (Quark), Sirolimus™ (Rapamycin), ATG003; Regeneron™ (VEGF Trap) or complement inhibitor (POT-4). The therapeutic agent can include a kinase inhibitor such as one or more of bevacizumab (monoclonal antibody), BIBW 2992 (small molecule targeting EGFR/Erb2), cetuximab (monoclonal antibody), imatinib (small molecule), trastuzumab (monoclonal antibody), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2NEGFR2, small molecule commercially available from Esai, Co.)

A variety of therapeutic agents can be delivered using the drug delivery implants described herein, including: anesthetics, analgesics, cell transport/mobility impending agents such as colchicine, vincristine, cytochalasin B and related compounds; antiglaucoma drugs including beta-blockers such as timolol, betaxolol, atenolol, and prostaglandins, lipid-receptor agonists or prostaglandin analogues such as bimatoprost, travoprost, latanoprost, unoprostone etc; alpha-adrenergic agonists, brimonidine or dipivefrine, carbonic anhydrase inhibitors such as acetazolamide, methazolamide, dichlorphenamide, diamox; and neuroprotectants such as nimodipine and related compounds.

Additional examples include antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; anti-fungal agents such as fluconazole, nitrofurazone, amphotericin B, ketoconazole, and related compounds; anti-viral agents such as trifluorothymidine, acyclovir, ganciclovir, DDI, AZT, foscarnet, vidarabine, trifluorouridine, idoxuridine, ribavirin, protease inhibitors and anti-cytomegalovirus agents; antiallergenics such as methapyriline; chlorpheniramine, pyrilamine and prophenpyridamine; anti-inflammatories such as hydrocortisone, dexamethasone, fluocinolone, prednisone, prednisolone, methylprednisolone, fluorometholone, betamethasone and triamcinolone; decongestants such as phenylephrine, naphazoline, and tetrahydrazoline; miotics, muscarinics and anti-cholinesterases such as pilocarpine, carbachol, di-isopropyl fluorophosphate, phospholine iodine, and demecarium bromide; mydriatics such as atropine sulfate, cyclopentolate, homatropine, scopolamine, tropicamide, eucatropine; sympathomimetics such as epinephrine and vasoconstrictors and vasodilators; Ranibizumab, Bevacizamab, and Triamcinolone.

Antiinflammatories, such as non-steroidal anti-inflammatories (NSAIDs) may also be delivered, such as cyclooxygenase-1 (COX-1) inhibitors (e.g., acetylsalicylic acid, for example ASPIRIN from Bayer AG, Leverkusen, Germany; ibuprofen, for example ADVIL from Wyeth, Collegeville, Pa.; indomethacin; mefenamic acid), COX-2 inhibitors (CELEBREX from Pharmacia Corp., Peapack, N.J.; COX-1 inhibitors), including a prodrug NEPAFENAC; immunosuppressive agents, for example Sirolimus (RAPAMUNE, from Wyeth, Collegeville, Pa.), or matrix metalloproteinase (MMP) inhibitors (e.g., tetracycline and tetracycline derivatives) that act early within the pathways of an inflammatory response. Anticlotting agents such as heparin, antifibrinogen, fibrinolysin, anti clotting activase, etc., can also be delivered.

Antidiabetic agents that may be delivered using the disclosed implants include acetohexamide, chlorpropamide, glipizide, glyburide, tolazamide, tolbutamide, insulin, aldose reductase inhibitors, etc. Some examples of anti-cancer agents include 5-fluorouracil, adriamycin, asparaginase, azacitidine, azathioprine, bleomycin, busulfan, carboplatin, carmustine, chlorambucil, cisplatin, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, fluoxymesterone, flutamide, goserelin, hydroxyurea, ifosfamide, leuprolide, levamisole, lomustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine.

Hormones, peptides, steroids, nucleic acids, saccharides, lipids, glycolipids, glycoproteins, and other macromolecules can be delivered using the present implants. Examples include: endocrine hormones such as pituitary, insulin, insulin-related growth factor, thyroid, growth hormones; heat shock proteins; immunological response modifiers such as muramyl dipeptide, cyclosporins, interferons (including $\alpha$, $\beta$, and $\gamma$ interferons), interleukin-2, cytokines, FK506 (an epoxy-pyrido-oxaazcyclotricosine-tetrone, also known as Tacrolimus), tumor necrosis factor, pentostatin, thymopentin, transforming factor beta2, erythropoetin; antineogenesis proteins (e.g., anti-VEGF, Interferons), among others and anticlotting agents including anticlotting activase. Further examples of macromolecules that can be delivered include monoclonal antibodies, brain nerve growth factor (BNGF), ciliary nerve growth factor (CNGF), vascular endothelial growth factor (VEGF), and monoclonal antibodies directed against such growth factors. Additional examples of immunomodulators include tumor necrosis factor inhibitors such as thalidomide.

In addition, nucleic acids can also be delivered wherein the nucleic acid may be expressed to produce a protein that may have a variety of pharmacological, physiological or immunological activities. Thus, the above list of drugs is not meant to be exhaustive. A wide variety of drugs or agents may be used in the present invention, without restriction on molecular weight, etc.

Other agents include anti-coagulant, an anti-proliferative, imidazole antiproliferative agent, a quinoxaline, a phsophonylmethoxyalkyl nucleotide analog, a potassium channel blocker, and/or a synthetic oligonucleotide, 5-[1-hydroxy-2-[2-(2-methoxyphenoxyl) ethylamino] ethyl]-2-methylbenzenesulfonamide, a guanylate cyclase inhibitor, such as methylene blue, butylated hydroxyanisole, and/or N-methylhydroxylamine, 2-(4-methylaminobutoxy) diphenylmethane, apraclonidine, a cloprostenol analog or a fluprostenol analog, a crosslinked carboxy-containing polymer, a sugar, and water, a non-corneotoxic serine-threonine kinase inhibitor, a nonsteroidal glucocorticoid antagonist, miotics (e.g., pilocarpine, carbachol, and acetylcholinesterase inhibitors), sympathomimetics (e.g., epinephrine and dipivalylepinephxine), beta-blockers (e.g., betaxolol, levobunolol and timolol), carbonic anhydrase inhibitors (e.g., acetazolamide, methazolamide and ethoxzolamide), and prostaglandins (e.g., metabolite derivatives of arachidonic acid, or any combination thereof.

Additional examples of beneficial drugs that may be employed and the specific conditions to be treated or prevented are disclosed in Remington, supra; The Pharmacological Basis of Therapeutics, by Goodman and Gilman, 19th edition, published by the MacMillan Company, London; and The Merck Index, 13th Edition, 1998, published by Merck & Co., Rahway, N.J., which is incorporated herein by reference.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A therapeutic device comprising:
   a housing configured to be positioned at least partially within a vitreous of the eye upon implantation, the housing comprising a reservoir extending between a proximal end region of the housing and a distal end region of the housing, the distal end region defining an outlet from the reservoir having a rigid porous structure positioned within the outlet and, the reservoir having a volume sized to contain one or more therapeutic agents for delivery through the outlet into the eye for an extended period of time;
   a proximal retention structure positioned near the proximal end region of the housing, the retention structure comprising a narrowed portion and a flanged portion extending proximally from the narrowed portion, wherein an access opening of the proximal retention structure extends through the retention structure into the reservoir;
   a septum positioned within the access opening, the septum having a first region positioned within at least a portion of the flanged portion and a second region located distal to the first region positioned at least in part within the narrowed portion; and
   a cover encapsulating at least the flanged portion of the proximal retention structure and bonded to an upper surface of the septum.

2. The device of claim 1, wherein the cover additionally encapsulates at least the proximal end region of the housing.

3. The device of claim 1, wherein the cover additionally encapsulates and bonds to an upper end portion of the access opening.

4. The device of claim 1, further comprising one or more surface features extending within at least an upper surface of the flanged portion of the proximal retention structure.

5. The device of claim 4, wherein the cover extends within and bonds to the one or more surface features.

6. The device of claim 5, wherein the one or more surface features comprises at least a through-hole extending from the upper surface to a lower surface of the flanged portion.

7. The device of claim 1, wherein the cover and the septum are configured to be penetrated with a needle during filling of the reservoir chamber and to re-seal upon removal of the needle.

8. The device of claim 1, wherein the septum is pre-molded and the cover is over-molded.

9. The device of claim 8, wherein the septum is a soft, high strength material and the cover is a high durometer material.

10. The device of claim 9, wherein the material of the septum is a liquid injection molding silicone elastomer and the material of the cover is a translucent, liquid silicone rubber.

11. The device of claim 9, wherein the access opening is formed of a material more rigid than the material of the septum.

12. The device of claim 11, wherein the septum is under a radial compressive force due to being over-sized relative to the access opening and held by the access opening in an adhesion-free manner.

13. The device of claim 12, wherein the radial compressive force encourages re-sealing of the septum after penetration and removal of a needle from the septum.

14. The device of claim 13, wherein the cover prevents withdrawal of the penetrable barrier in a proximal direction upon removal of the needle from the septum.

15. The device of claim 1, wherein the septum further comprises surface treatments on an external surface.

16. The device of claim 1, wherein the cover has a thickness that is 0.007"-0.025".

17. The device of claim 1, wherein the cover extends beyond an outer diameter of the flanged portion and upward from an upper surface of the flanged portion providing a higher profile to the retention structure.

18. The device of claim 1, wherein the septum further comprises a distal region that is flared and positioned within a proximal end region of the reservoir.

19. The device of claim 1, wherein the septum further comprises one or more tabs, a flared skirt, flange, rib or other feature.

20. The device of claim 1, wherein the upon being implanted in the eye, the flanged portion extends along the sclera, the narrowed portion extends trans-sclerally and at least a portion of the reservoir in the housing is located within a vitreous humor of the eye.

* * * * *